US008808276B2

(12) United States Patent
Boyden et al.

(10) Patent No.: US 8,808,276 B2
(45) Date of Patent: Aug. 19, 2014

(54) ADAPTIVE DISPENSATION IN A DIGESTIVE TRACT

(75) Inventors: Edward S. Boyden, Cambridge, MA (US); Roderick A. Hyde, Redmond, WA (US); Muriel Y. Ishikawa, Livermore, CA (US); Jordin T. Kare, Seattle, WA (US); Robert Langer, Newton, MA (US); Eric C. Leuthardt, St. Louis, MO (US); Dennis J. Rivet, Portsmouth, VA (US); Michael A. Smith, Phoenix, AZ (US); Charles Whitmer, North Bend, WA (US); Lowell L. Wood, Jr., Bellevue, WA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1153 days.

(21) Appl. No.: 10/536,126

(22) Filed: Oct. 23, 2007

(65) Prior Publication Data

US 2009/0192449 A1    Jul. 30, 2009

(51) Int. Cl.
*A61K 9/22* (2006.01)
*A61M 31/00* (2006.01)

(52) U.S. Cl.
USPC .......................................... 604/890.1; 604/65

(58) Field of Classification Search
CPC ........ A61B 5/07; A61B 5/14532; A61B 5/42; A61M 31/002
USPC .......... 604/65, 890.1, 67, 99.02, 164.02, 208, 604/246, 537, 30, 891.1; 424/9.1, 451; 600/118
See application file for complete search history.

(56) References Cited

U.S. PATENT DOCUMENTS

| | | | |
|---|---|---|---|
| 4,096,238 A | 6/1978 | Zaffaroni et al. |
| 4,207,890 A | 6/1980 | Mamajek et al. |
| 4,522,625 A | 6/1985 | Edgren |
| 4,595,583 A | 6/1986 | Eckenhoff et al. |
| 4,735,804 A | 4/1988 | Caldwell et al. |
| 4,758,436 A | 7/1988 | Caldwell et al. |
| 4,878,905 A | 11/1989 | Blass |
| 4,925,446 A | 5/1990 | Garay et al. |
| 5,198,229 A | 3/1993 | Wong et al. |
| 5,318,557 A | 6/1994 | Gross |
| 5,354,264 A | 10/1994 | Bae et al. |
| 5,576,025 A | 11/1996 | Akiyama et al. |

(Continued)

FOREIGN PATENT DOCUMENTS

WO    WO 2006/077527 A1    7/2006
WO    WO 2007/013059 A2    2/2007

OTHER PUBLICATIONS

Duchene, D. et al.; "Pharaceutical and Medical Aspects of Bioadhesive Systems for Drug Administration"; Drug Development and Industrial Pharmacy; 1988; pp. 283-318; vol. 14, No. 2 & 3; Marcel Dekker, Inc.

(Continued)

*Primary Examiner* — Kami A Bosworth
*Assistant Examiner* — Imani Hayman

(57) ABSTRACT

Systems and methods are described for implementing a bioactive material selection from within a digestive tract and transmitting a wireless signal indicating at least the bioactive material selection from within the digestive tract.

33 Claims, 10 Drawing Sheets

(56) References Cited

U.S. PATENT DOCUMENTS

| | | |
|---|---|---|
| 5,797,898 A | 8/1998 | Santini, Jr. et al. |
| 5,879,325 A | 3/1999 | Lindstrom et al. |
| 5,938,654 A | 8/1999 | Wong et al. |
| 6,120,803 A | 9/2000 | Wong et al. |
| 6,240,312 B1 | 5/2001 | Alfano et al. |
| 6,283,953 B1 | 9/2001 | Ayer et al. |
| 6,285,897 B1 | 9/2001 | Kilcoyne et al. |
| 6,425,904 B1 | 7/2002 | Lemelson |
| 6,428,813 B1 | 8/2002 | Akiyama et al. |
| 6,475,521 B1 | 11/2002 | Timmins et al. |
| 6,535,764 B2 | 3/2003 | Imran et al. |
| 6,547,776 B1 | 4/2003 | Gaiser et al. |
| 6,582,720 B1 | 6/2003 | Inagi et al. |
| 6,632,655 B1 | 10/2003 | Mehta et al. |
| 6,656,194 B1 | 12/2003 | Gannoe et al. |
| 6,656,464 B2 | 12/2003 | Kondo |
| 6,677,313 B1 | 1/2004 | Mathiowitz et al. |
| 6,689,056 B1 | 2/2004 | Kilcoyne et al. |
| 6,776,165 B2 | 8/2004 | Jin |
| 6,797,268 B2 | 9/2004 | Kodama et al. |
| 6,797,283 B1 | 9/2004 | Edgren et al. |
| 6,911,004 B2 | 6/2005 | Kim et al. |
| 6,929,636 B1 * | 8/2005 | von Alten ............... 604/890.1 |
| 6,939,290 B2 | 9/2005 | Iddan |
| 6,942,771 B1 | 9/2005 | Kayyem |
| 6,950,690 B1 | 9/2005 | Meron et al. |
| 6,958,034 B2 | 10/2005 | Iddan |
| 6,960,356 B1 | 11/2005 | Talwar et al. |
| 6,994,095 B2 | 2/2006 | Burnett |
| 7,016,735 B2 | 3/2006 | Imran et al. |
| 7,033,322 B2 | 4/2006 | Silver |
| 7,041,083 B2 | 5/2006 | Chu et al. |
| 7,083,578 B2 | 8/2006 | Lewkowicz et al. |
| 7,097,851 B1 | 8/2006 | Takada |
| 7,105,300 B2 | 9/2006 | Parce et al. |
| 7,105,810 B2 | 9/2006 | Kameoka et al. |
| 7,160,258 B2 | 1/2007 | Imran et al. |
| 7,182,957 B2 | 2/2007 | Zentner et al. |
| 7,220,237 B2 | 5/2007 | Gannoe et al. |
| 7,353,067 B1 | 4/2008 | Helland et al. |
| 7,857,767 B2 | 12/2010 | Ferren et al. |
| 8,038,659 B2 | 10/2011 | Boyden et al. |
| 2002/0012651 A1 | 1/2002 | Loeb |
| 2002/0055734 A1 | 5/2002 | Houzego et al. |
| 2002/0129443 A1 | 9/2002 | Di Cecco |
| 2002/0137803 A1 | 9/2002 | Kirkland |
| 2002/0151776 A1 | 10/2002 | Shawgo et al. |
| 2002/0173770 A1 | 11/2002 | Flory et al. |
| 2003/0023150 A1 | 1/2003 | Yokoi et al. |
| 2003/0092964 A1 | 5/2003 | Kim et al. |
| 2003/0113371 A1 | 6/2003 | Dhawan et al. |
| 2003/0191476 A1 | 10/2003 | Smit |
| 2003/0216622 A1 | 11/2003 | Meron et al. |
| 2003/0232078 A1 | 12/2003 | Dong et al. |
| 2004/0109894 A1 | 6/2004 | Shefer et al. |
| 2004/0121015 A1 | 6/2004 | Chidlaw et al. |
| 2004/0158194 A1 | 8/2004 | Wolff et al. |
| 2004/0214311 A1 | 10/2004 | Levy |
| 2004/0220498 A1 | 11/2004 | Li et al. |
| 2004/0224019 A1 | 11/2004 | Shefer et al. |
| 2004/0236180 A1 | 11/2004 | Uchiyama et al. |
| 2005/0019407 A1 | 1/2005 | Sowden et al. |
| 2005/0037312 A1 | 2/2005 | Uchida |
| 2005/0058701 A1 | 3/2005 | Gross et al. |
| 2005/0064027 A1 | 3/2005 | Jacob et al. |
| 2005/0065571 A1 | 3/2005 | Imran |
| 2005/0100937 A1 | 5/2005 | Holmes |
| 2005/0147559 A1 | 7/2005 | von Alten |
| 2005/0158246 A1 | 7/2005 | Takizawa et al. |
| 2005/0165272 A1 | 7/2005 | Okada et al. |
| 2005/0201974 A1 | 9/2005 | Schestopol et al. |
| 2005/0222537 A1 | 10/2005 | Dinsmoor et al. |
| 2005/0234399 A1 | 10/2005 | Wood, Jr. |
| 2005/0245906 A1 | 11/2005 | Makower et al. |
| 2005/0246037 A1 | 11/2005 | Starkebaum |
| 2005/0249799 A1 | 11/2005 | Jacob et al. |
| 2005/0277912 A1 | 12/2005 | John |
| 2006/0003007 A1 | 1/2006 | Odidi et al. |
| 2006/0045865 A1 | 3/2006 | Jacob et al. |
| 2006/0062852 A1 | 3/2006 | Holmes |
| 2006/0063974 A1 | 3/2006 | Uchiyama et al. |
| 2006/0099245 A1 | 5/2006 | Kumar et al. |
| 2006/0152309 A1 | 7/2006 | Mintchev et al. |
| 2006/0157067 A1 | 7/2006 | Saadat et al. |
| 2006/0167339 A1 | 7/2006 | Gilad et al. |
| 2006/0182738 A1 | 8/2006 | Holmes |
| 2006/0190019 A1 | 8/2006 | Gannoe et al. |
| 2006/0195015 A1 | 8/2006 | Mullick et al. |
| 2006/0241718 A1 | 10/2006 | Tyler et al. |
| 2006/0248698 A1 | 11/2006 | Hanson et al. |
| 2006/0289640 A1 | 12/2006 | Mercure et al. |
| 2007/0080658 A1 | 4/2007 | Farritor et al. |
| 2007/0088334 A1 | 4/2007 | Hillis et al. |
| 2007/0106213 A1 | 5/2007 | Spera et al. |
| 2007/0106226 A1 | 5/2007 | Croll et al. |
| 2007/0123809 A1 | 5/2007 | Weiss et al. |
| 2007/0161851 A1 | 7/2007 | Takizawa et al. |
| 2007/0178160 A1 | 8/2007 | Burnett |
| 2007/0213659 A1 | 9/2007 | Trovato et al. |
| 2007/0219405 A1 | 9/2007 | Uchiyama et al. |
| 2007/0225576 A1 | 9/2007 | Brown et al. |
| 2007/0225633 A1 | 9/2007 | Ferren et al. |
| 2007/0244388 A1 | 10/2007 | Sato et al. |
| 2007/0253761 A1 | 11/2007 | May |
| 2007/0255100 A1 | 11/2007 | Barlow et al. |
| 2007/0265496 A1 | 11/2007 | Kawano et al. |
| 2008/0194912 A1 * | 8/2008 | Trovato et al. ............... 600/118 |
| 2008/0214619 A1 | 9/2008 | Wolfe et al. |
| 2009/0306633 A1 * | 12/2009 | Trovato et al. ............. 604/891.1 |

OTHER PUBLICATIONS

Quirini, Marco et al.; "Design of a Pill-Sized 12-Legged Endoscopic Capsule Robot"; IEEE International Conference on Robotics and Automation in Rome, Italy; Apr. 10-14, 2007; pp. 1856-1862; vol. ThA7.2; IEEE.

Rentschler, Mark E. et al.; "Natural Orifice Surgery With an Endoluminal Mobile Robot"; SAGES Meeting; 2006; pp. 1-14; located at: http://robots.unl.edu/Files/Papers2/Rentschler_Natural_Orifice_Robot_with figures.pdf.

Excerpt from the American Heritage Dictionary of the English Language; bearing a date of 2009; Printed on Jan. 19, 2011; located at: http://education.yahoo.com/reference/dictionary/entry/moor; total of 2 pages (as provided by examiner).

* cited by examiner

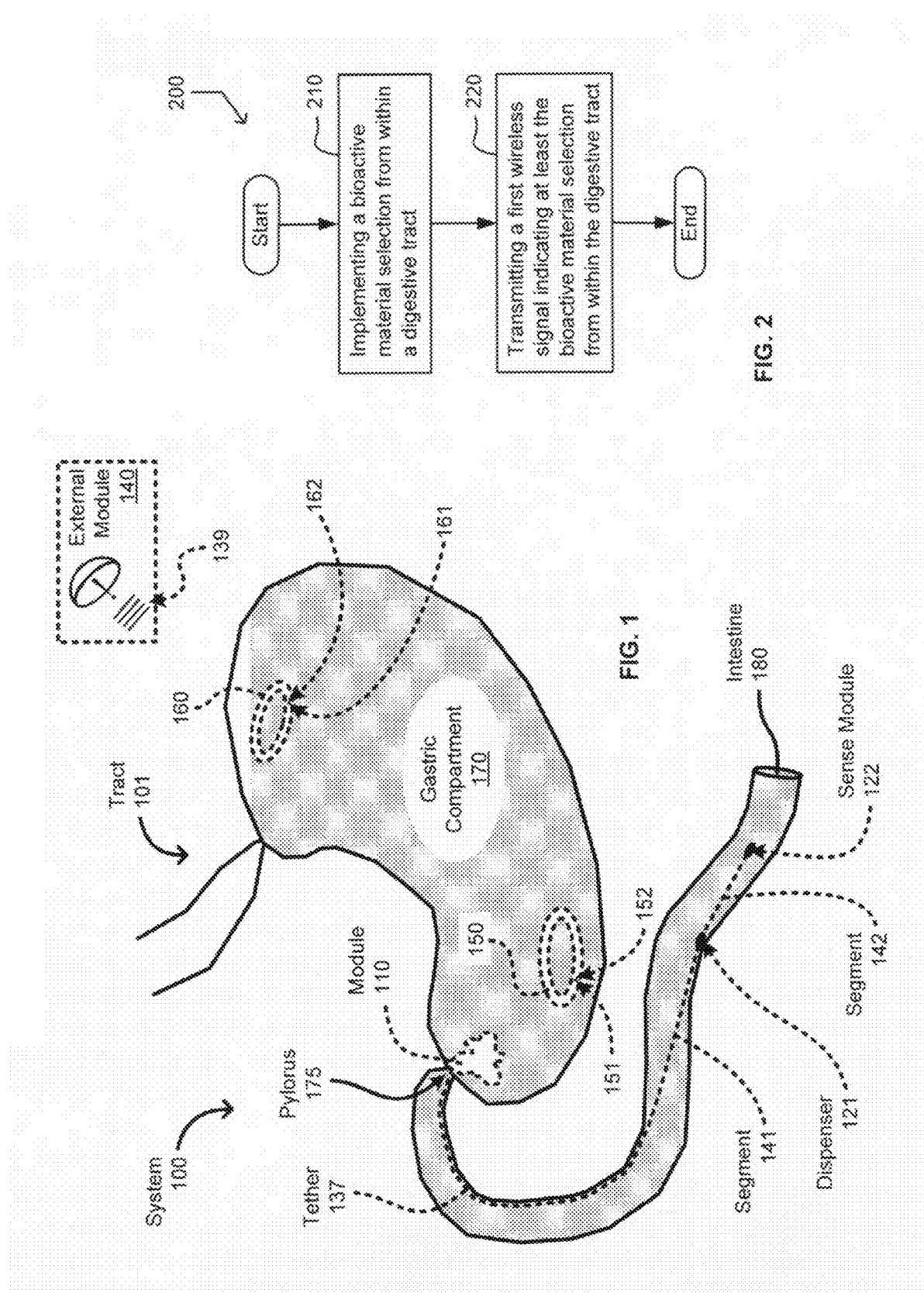

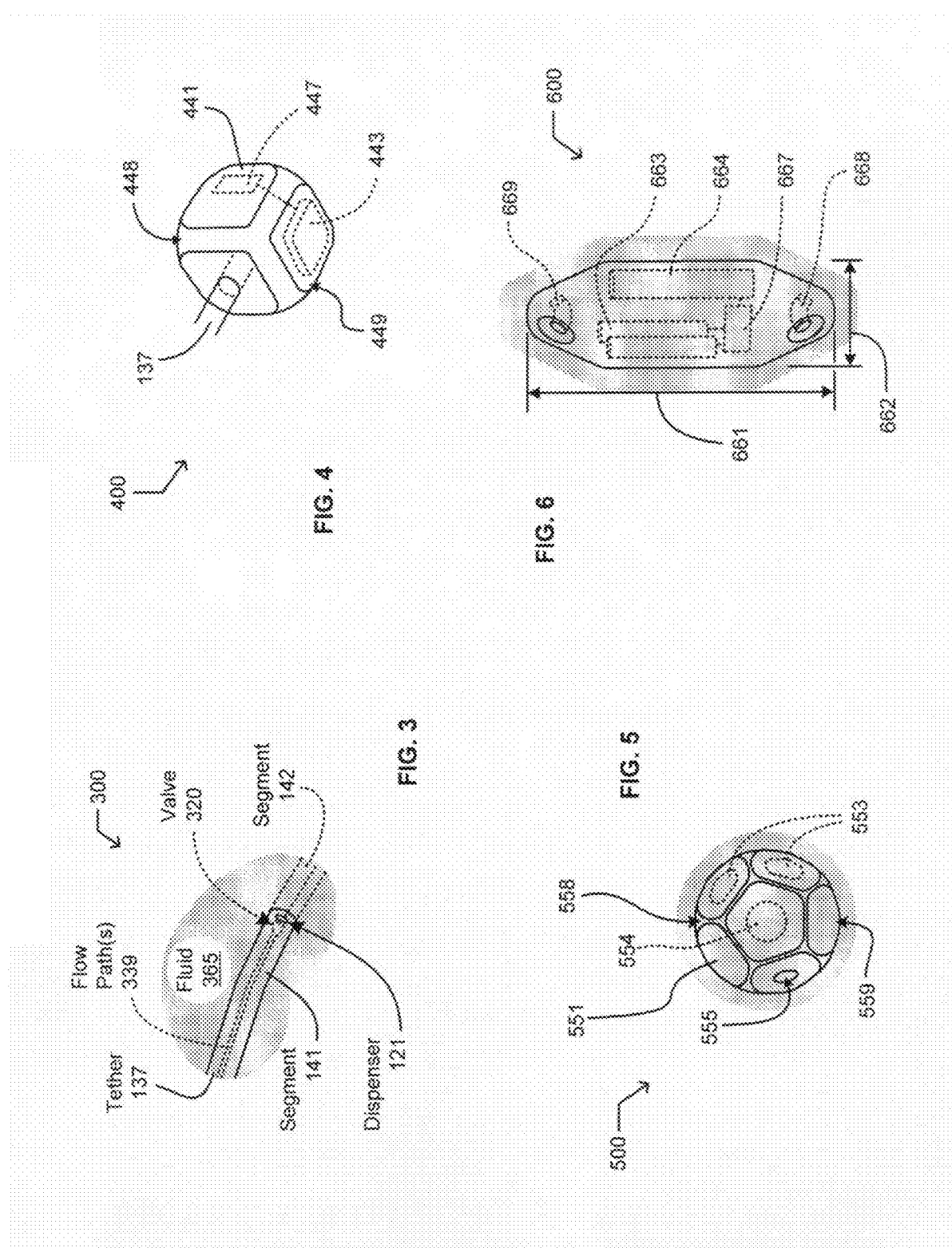

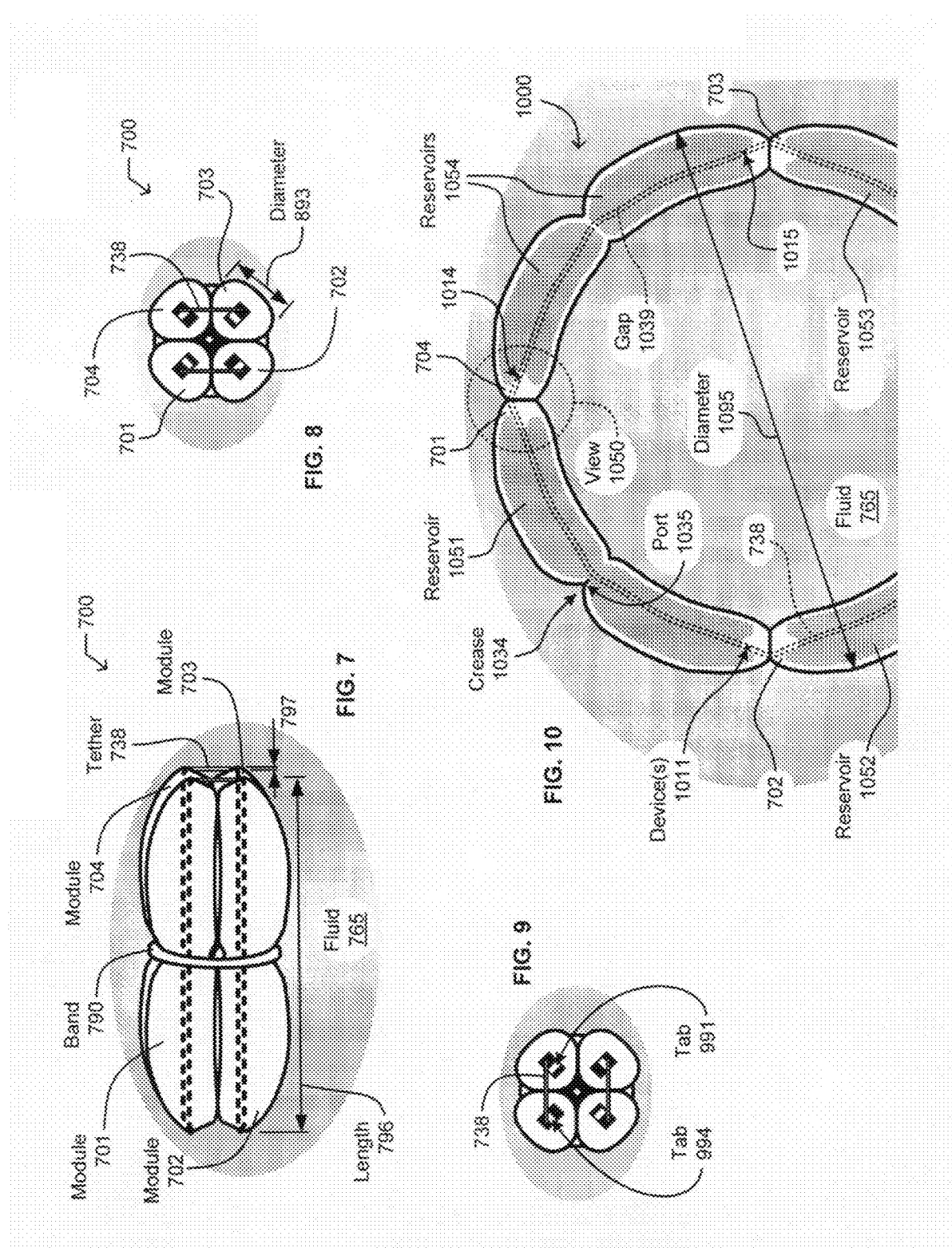

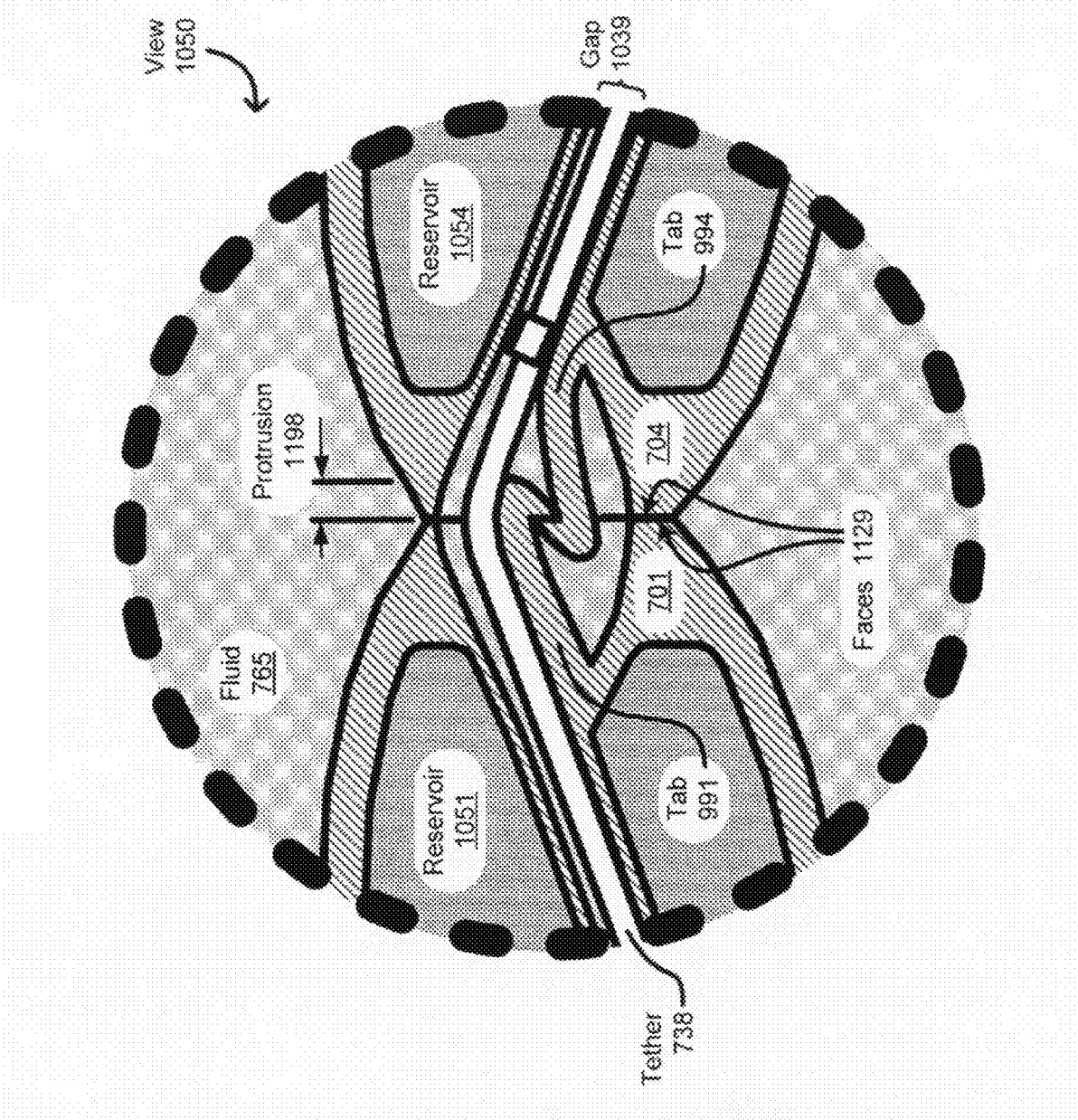

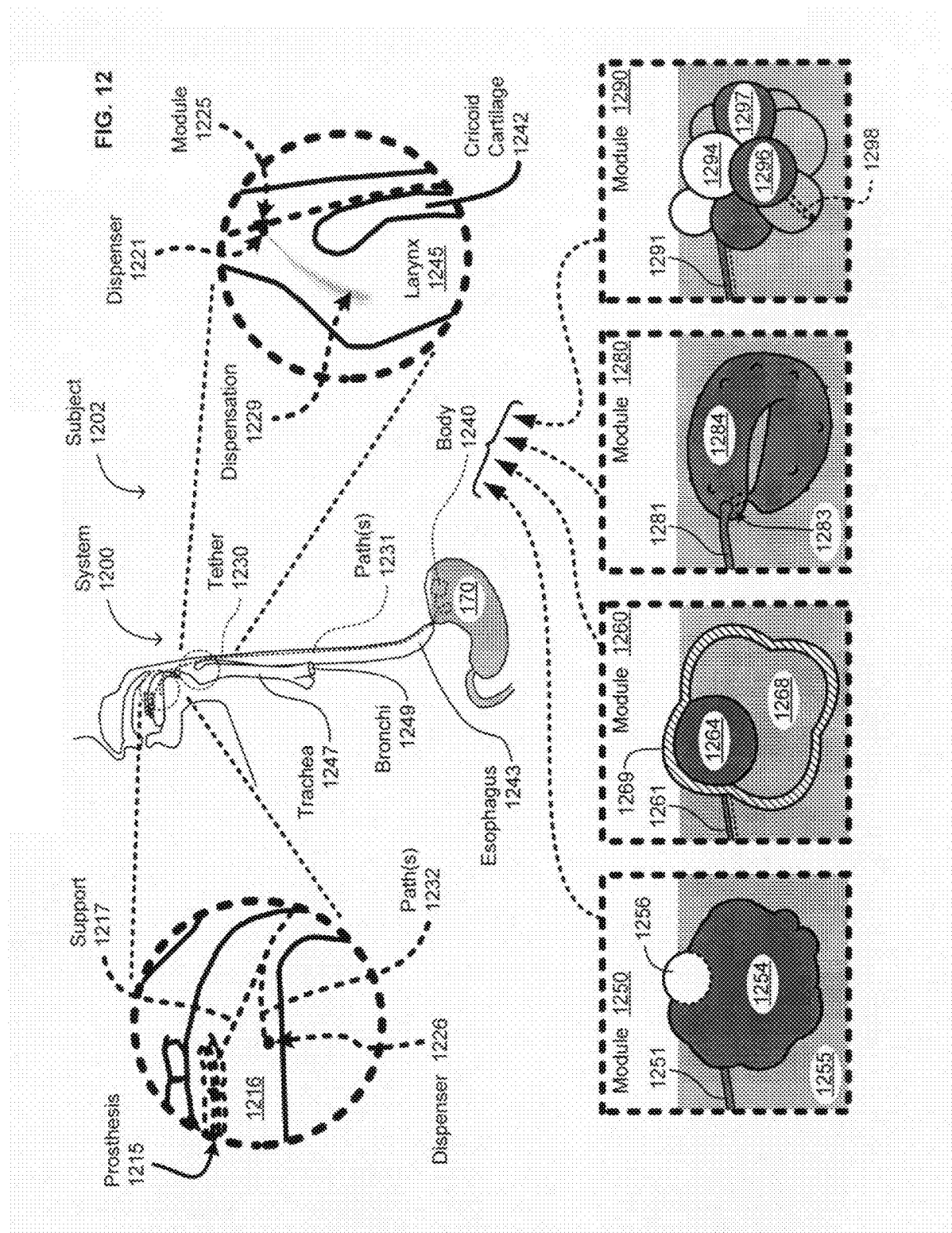

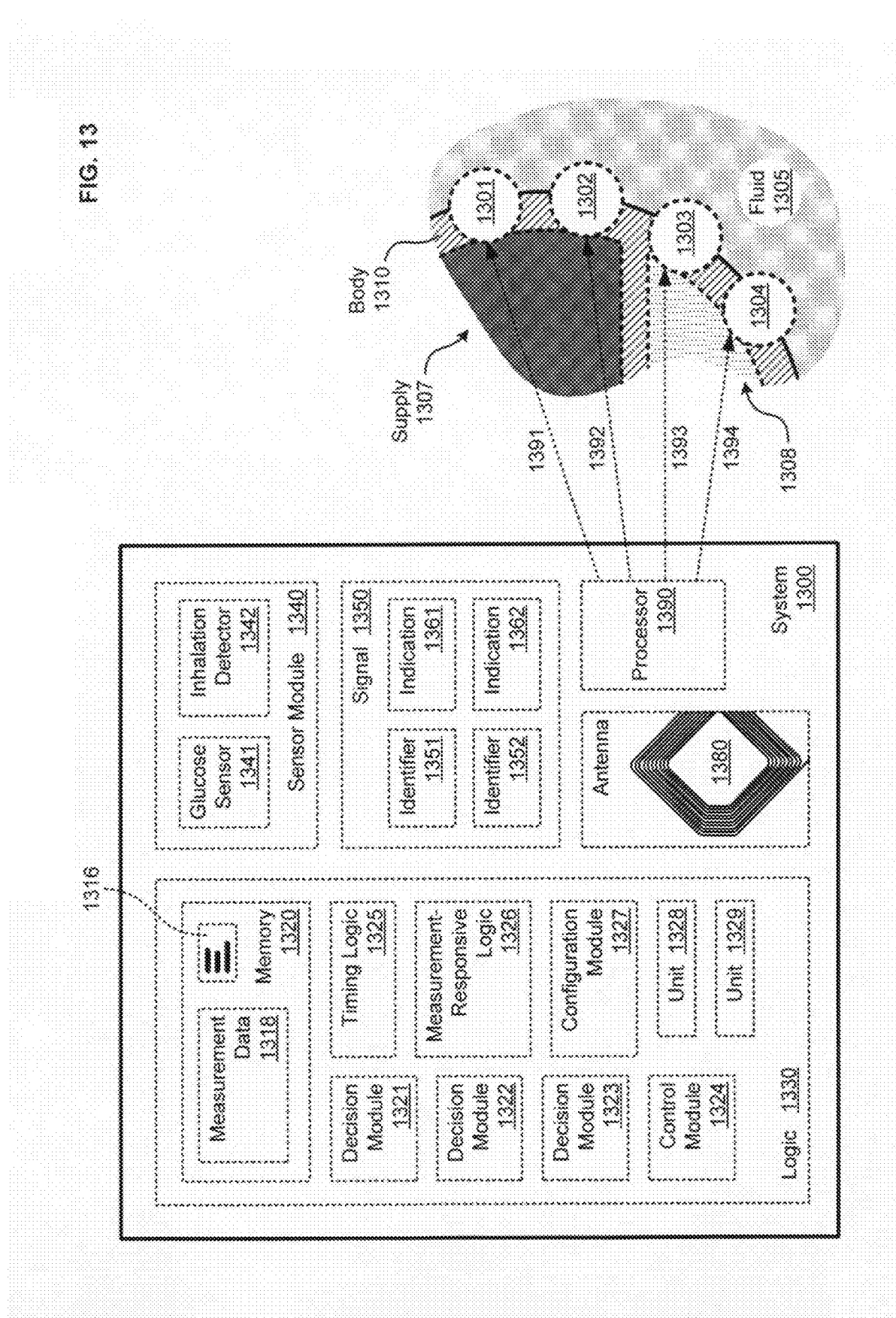

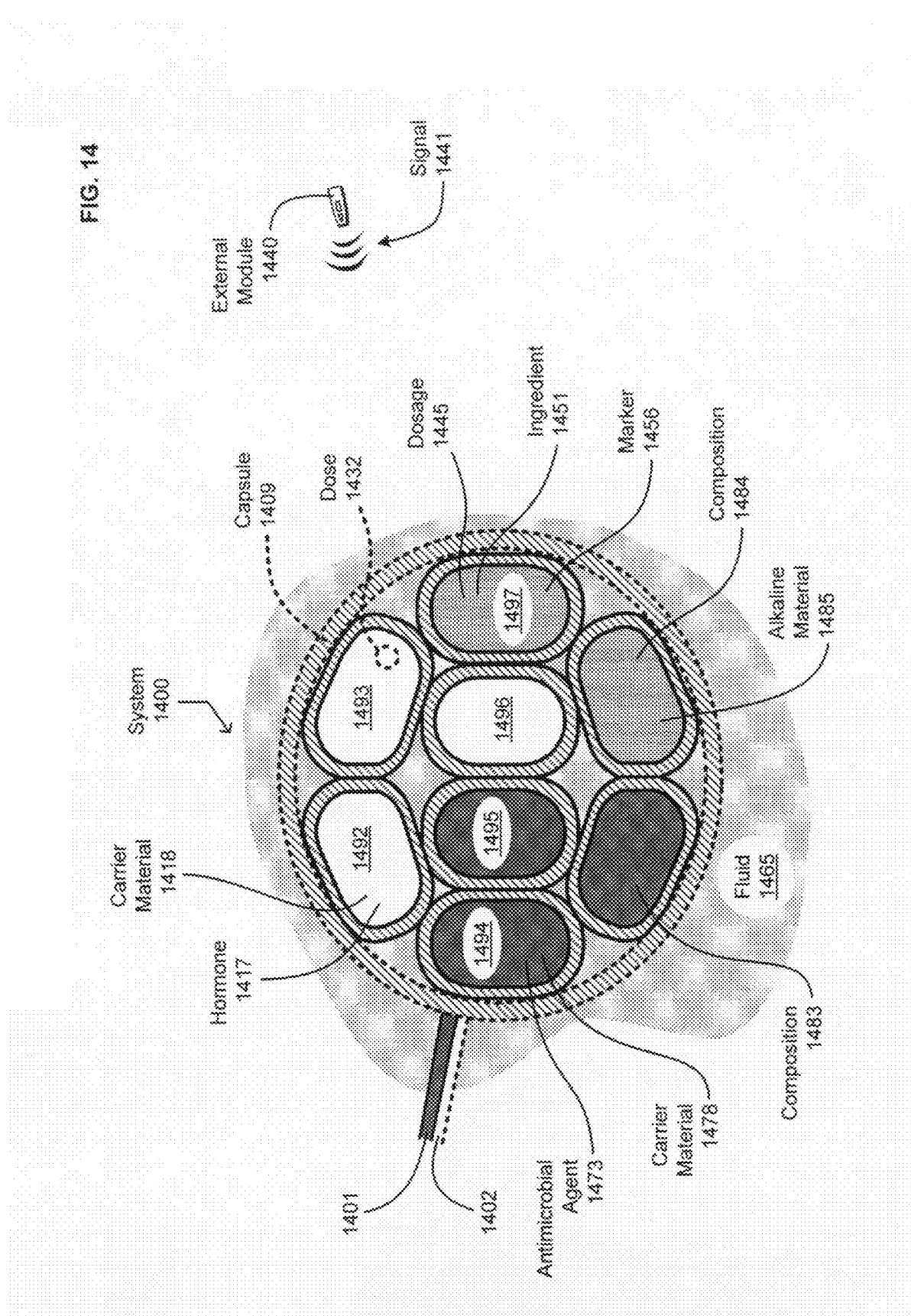

ADAPTIVE DISPENSATION IN A DIGESTIVE TRACT

SUMMARY

In one aspect, a method includes but is not limited to implementing a bioactive material selection from within a digestive tract and transmitting a first wireless signal indicating at least the bioactive material selection from within the digestive tract. In addition to the foregoing, other method aspects are described in the claims, drawings, and text forming a part of the present disclosure.

In one or more various aspects, related systems include but are not limited to circuitry and/or programming for effecting the herein-referenced method aspects; the circuitry and/or programming can be virtually any combination of hardware, software, and/or firmware configured to effect the herein-referenced method aspects depending upon the design choices of the system designer.

In one aspect, a system includes but is not limited to circuitry for implementing a bioactive material selection from within a digestive tract and circuitry for transmitting a first wireless signal indicating at least the bioactive material selection from within the digestive tract. In addition to the foregoing, other system aspects are described in the claims, drawings, and text forming a part of the present disclosure.

In addition to the foregoing, various other method and/or system and/or program product and/or physical carrier aspects are set forth and described in the teachings such as text (e.g., claims and/or detailed description) and/or drawings of the present disclosure.

The foregoing is a summary and thus contains, by necessity, simplifications, generalizations and omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE FIGURES

FIG. 1 depicts an exemplary environment in which one or more technologies may be implemented.

FIG. 2 depicts a high-level logic flow of an operational process.

FIGS. 3-15 depict respective environments in which one or more mechanical, electromechanical or other technologies as described herein may be implemented.

DETAILED DESCRIPTION

Figure 15:
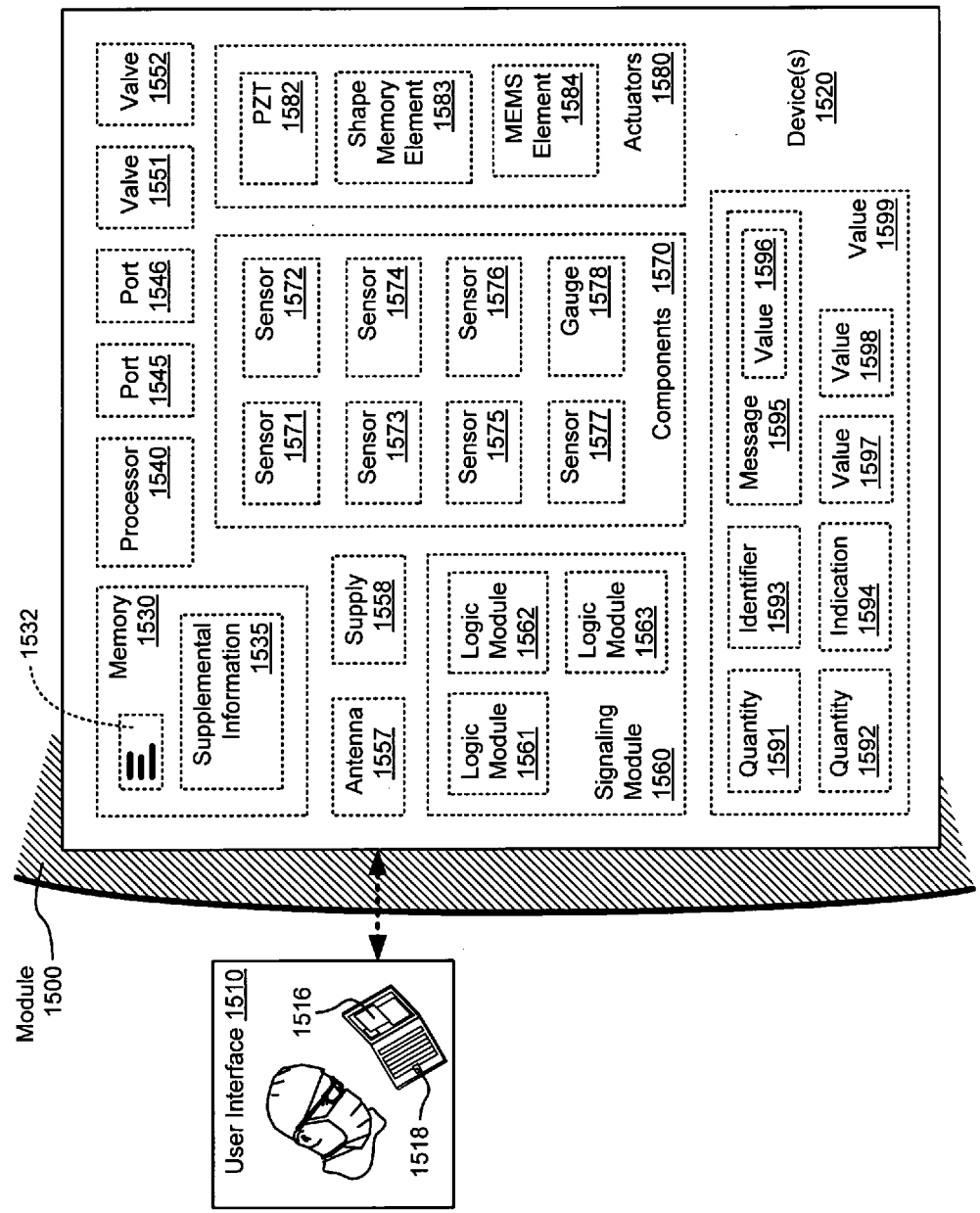

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

In the following detailed description, reference is made to the accompanying drawings, which form a part hereof. The use of the same symbols in different drawings typically indicates similar or identical items. The illustrative embodiments described in the detailed description, drawings, and claims are not meant to be limiting. Other embodiments may be utilized, and other changes may be made, without departing from the spirit or scope of the subject matter presented here.

Following are a series of systems and flowcharts depicting implementations of processes. For ease of understanding, the flowcharts are organized such that the initial flowcharts present implementations via an initial "big picture" viewpoint and thereafter the following flowcharts present alternate implementations and/or expansions of the "big picture" flowcharts as either sub-steps or additional steps building on one or more earlier-presented flowcharts. Those having skill in the art will appreciate that the style of presentation utilized herein (e.g., beginning with a presentation of a flowchart(s) presenting an overall view and thereafter providing additions to and/or further details in subsequent flowcharts) generally allows for a rapid and easy understanding of the various process implementations. In addition, those skilled in the art will further appreciate that the style of presentation used herein also lends itself well to modular and/or object-oriented program design paradigms.

With reference now to FIG. 1, shown is a vicinity of a gastric compartment 170 in a digestive tract 101 of a subject (human or otherwise) that may serve as a context for introducing one or more processes and/or devices described herein. As shown system 100 may (optionally) include one or more instances of module 110 each having one or more tethers 137 or other portions extending through some of intestine 180 and configured to anchor at pylorus 175. System 100 may likewise include one or more instances of modules 150 dense enough to rest near the bottom of gastric compartment 170 and/or modules 160 buoyant enough to float within gastric compartment 170, any or all of which may be configured with one or more dispensers 151, 161 and/or control modules 152, 162. Many suitable structures are described herein and in U.S. patent application Ser. No. 11/975,371, titled ["Disintegrating Digestive Tract Interaction System," filed 17 Oct. 2007], also by Boyden et al., incorporated by reference to the extent not inconsistent herewith. In some such embodiments, each tether 137 of interest may comprise one or more segments 141 directly or indirectly coupling a reservoir-containing module (such as module 110 or module 150) with one or more of its dispensers 121. In some variants, moreover, such modules 110, 150, 160 may comprise control modules 152, 162 or other circuitry operable for handling one or more wireless signals 139 passing to or from external module 140. Alternatively or additionally, each tether 137 of interest may comprise one or more segments 142 directly or indirectly coupling a reservoir-containing module with one or more of its sense modules 122. In various embodiments described herein, such dispensers, sensor modules, and support structures therefore may each be inside, outside, or spanning the gastric compartment or, in some cases, extending outside the digestive tract. In some variants, one or more such segments 141, 142 configured to support such devices in intestine 180 comprise structures of a (positive) solubility in a gastric compartment low enough to remain in situ for more than a day (or month or year), as described herein. Alternatively or additionally one or more such modules 110, 150, 160 may include two or more (component) modules similarly tethered together as described herein.

In some embodiments, one or more such modules 110, 150, 160 or other fluid-exposed structures depicted herein may comprise at least an external layer primarily made of one or more water insoluble polymers such as cellulose derivatives (i.e., ethylcellulose), polyvinyl acetate, neutral copolymers based on ethyl acrylate and methylmethacrylate, copolymers of acrylic and methacrylic acid esters with quaternary ammonium groups, or the like. In some embodiments, polymers used in forming such low-solubility elements may be plasticized. Examples of plasticizers that may be used for this purpose include, but are not limited to, triacetin, tributyl citrate, triethyl citrate, acetyl tri-n-butyl citrate diethyl phthalate, castor oil, dibutyl sebacate, acetylated monoglycerides, or the like and/or substantially any combination thereof. In some embodiments, one or more such plasticizers may be present at about 3 to 30 weight percent and more typically about 10 to 25 weight percent based on the polymer to which the plasticizer is added. The type of plasticizer and its content depends on the polymer or polymers and/or the nature of the coating system.

In some embodiments, water-soluble nonionic polysaccharide derivatives may be used to wrap one or more therapeutic agents or other soluble structures for rapid release. For example, hydroxypropylmethylcellulose, hydroxypropylcellulose, and/or sodium carboxymethylcellulose may be used. Such polymers form coatings that quickly dissolve in digestive fluids or water and have a high permeability. Accordingly, in some embodiments, such polymers may be used for rapid release responsive to ingestion.

In some embodiments, one or more therapeutic agents or other structures may be wrapped in a wrapper that provides for sustained release of the one or more therapeutic agents. For example, one or more therapeutic agents may be released continuously over twelve hours through use of wrappers constructed from ethyl cellulose and an ethyl acrylate-methyl methacrylate-ethyl trimethylammoniumchloride methacrylate copolymer as the release controlling wrapper. Existing methods and materials that may be used to prepare such wrappers are known by those skilled in the art and are commercially available (i.e., Rohm Pharma, Piscataway, N.J.; U.S. Pat. Nos. 6,656,507; 7,048,945; 7,056,951; hereby incorporated by reference to the extent not inconsistent herewith).

With reference now to FIG. 2, there is shown a high-level logic flow 200 of an operational process. Flow 200 includes operation 210—implementing a bioactive material selection from within a digestive tract (e.g. dispenser 151 becoming active in lieu of dispenser 161). In some embodiments, material selections are "implemented" by triggering or performing a selective dispensation of one or more materials available for dispensation. This can occur, for example, in an embodiment in which dispenser 151 contains an antibiotic and/or a proton inhibitor, in which dispenser 151 dispenses continuously over a period of about a week or more, and in which external module 140 has signaled dispenser 151 or its contents with an external material selection. Alternatively or additionally, dispenser 151 may (optionally) be configured to activate automatically in response to an ingested marker material, to prolonged immersion in an acidic environment, or to other detected conditions warranting an internal material selection. In some variants, two or more bioactive material sources may be cooperatively controlled, such as in an embodiment in which control module 152 activates dispenser 151 only in response to a selection generated by another control module in a vicinity of tract 101.

In light of teachings herein, numerous existing techniques may be applied for preparing appropriate drug delivery formulations as described herein without undue experimentation. See, e.g., U.S. Pat. No. 7,189,414 ("Controlled release oral drug delivery system"); U.S. Pat. No. 7,125,566 ("Particulate drug-containing products and method of manufacture"); U.S. Pat. No. 7,097,851 ("Oral formulation for gastrointestinal drug delivery"); U.S. Pat. No. 6,960,356 ("Orally administered drug delivery system providing temporal and spatial control"); U.S. Pat. No. 6,699,503 ("Hydrogel-forming sustained-release preparation"); U.S. Pat. No. 6,644,517 ("Stem configuration to reduce seal abrasion in metered dose aerosol valves"); U.S. Pat. No. 6,638,534 ("Preparation capable of releasing drug at target site in intestine"); U.S. Pat. No. 6,582,720 ("Medicinal compositions adhering to stomach/duodenum"); U.S. Pat. No. 6,475,521 ("Biphasic controlled release delivery system for high solubility pharmaceuticals and method"); U.S. Pat. No. 6,399,086 ("Pharmaceutical preparations for the controlled release of beta-lactam antibiotics"); U.S. Pat. No. 6,240,917 ("Aerosol holding chamber for a metered-dose inhaler"); U.S. Pat. No. 6,116,237 ("Methods of dry powder inhalation"); U.S. Pat. No. 6,060,069 ("Pulmonary delivery of pharmaceuticals"); U.S. Pat. No. 5,989,217 ("Medicine administering device for nasal cavities"); U.S. Pat. No. 5,906,587 ("Apparatus and method for the treatment of esophageal varices and mucosal neoplasms"); U.S. Pat. No. 5,837,261 ("Viral vaccines"); U.S. Pat. No. 5,823,180 ("Methods for treating pulmonary vasoconstriction and asthma"); U.S. Pat. No. 5,645,051 ("Unit dose dry powder inhaler"). Those skilled in the art will also recognize how to apply numerous existing techniques for taking provisional, alternate, overlapping, or completion actions relating to such applications as exemplified herein without undue experimentation, in light of these teachings. One or more wireless signals 139 may be used directly to control some or all aspects of activating one or more such dispensers 121, 161 on a selective basis, for example. Sense module 122 may be configured to signal one or more dispensers 121, 151 to reduce, postpone, or forego an output of a bioactive material, for example, in response to a high level of such materials (or metabolites or other indicators thereof) being detected. Alternatively or additionally, such functionality may be configured to depend on whether one or more modules 110, 150, 160 are depleted, not yet deployed, disintegrated, or in some other condition that may prevent effective operation.

In some cases, such functionality may likewise depend upon one or more other determinants in substantially any desired combination: upon whether excessive acidity or some other symptom has been detected directly, upon whether an a priori attribute of a subject makes a bioactive material unnecessary and/or unsafe for a potential dispensation, upon whether the subject has contemporaneously requested or otherwise authorized a pain reliever, upon how long a time has elapsed since a prior dispensation, upon other state or timing factors as described herein, upon how much remains of a reservoir or other bioactive material supply, upon whether a subject has taken alcohol or any other controlled substance, or upon other determinants such as are known in the art. Such combinations may each be effectuated by comparative, arithmetic, conjunctive, or other operators relating each pairing of determinants described herein, for example.

Flow 200 also includes operation 220—transmitting a first wireless signal indicating at least the bioactive material selection from within the digestive tract (e.g. control module 152 transmitting one or more wireless signals 139 confirming an activation of dispenser 151). This can occur, for example, in response to external module 140 requesting such information and/or providing communication-enabling power remotely to control module 152. Alternatively or additionally, control module 152 may provide a serial number, a model number, an ingredient recitation, a timestamp, a dosage, or other such supplemental information in wireless signal 139.

In light of these teachings, numerous existing techniques may be applied for performing appropriate telemetry or otherwise handling wireless signals as described herein without undue experimentation. See, e.g., U.S. Pat. No. 7,262,020 ("Methods for comparing relative flux rates of two or more biological molecules in vivo through a single protocol"); U.S. Pat. No. 7,214,182 ("Wireless in-vivo information acquiring system, body-insertable device, and external device"); U.S. Pat. No. 7,160,258 ("Capsule and method for treating or diagnosing the intestinal tract"); U.S. Pat. No. 7,146,216 ("Implantable muscle stimulation device for treating gastrointestinal reflux disease"); U.S. Pat. No. 7,118,529 ("Method and apparatus for transmitting non-image information via an image sensor in an in vivo imaging system"); U.S. Pat. No. 6,929,636 ("Internal drug dispenser capsule medical device"); U.S. Pat. No. 6,632,655 ("Manipulation of microparticles in microfluidic systems"); U.S. Pat. No. 6,503,504 ("Delivery of bioactive compounds to an organism"); U.S. Pat. No. 6,411,842 ("Implant device for internal-external electromyographic recording, particularly for the in vivo study of electromotor activity of the digestive system"); U.S. Pat. No. 6,285,897 ("Remote physiological monitoring system"); U.S. Pat. No. 6,403,647 ("Pulsed administration of compositions for the treatment of blood disorders"); U.S. Pat. No. 6,360,123 ("Apparatus and method for determining a mechanical property of an organ or body cavity by impedance determination"); U.S. Pat. No. 6,329,153 ("Method for evaluating immunosuppressive regimens"); U.S. Pat. No. 5,985,129 ("Method for increasing the service life of an implantable sensor"); U.S. Pat. No. 5,779,631 ("Spectrophotometer for measuring the metabolic condition of a subject"); U.S. Pat. No. 5,569,186 ("Closed loop infusion pump system with removable glucose sensor"). Those skilled in the art will also recognize how to apply numerous existing techniques for taking provisional, alternate, overlapping, or completion actions relating to such applications as exemplified herein without undue experimentation, in light of these teachings. Sense module 122 may be configured to transmit one or more selection indications wirelessly, for example, or to communicate such information via a signal conduit to module 110, which subsequently transmits an audible or other wireless signal. In some variants, for example, module 110 includes a signal bearing conduit to a speaker in a subject's jaw or ear to notify the subject of a dispensation.

With reference now to FIG. 3, shown is a system 300 that may serve as a context for introducing one or more processes and/or devices described herein. As shown system 300 may include an optional configuration of tether 137 (of FIG. 1) comprising a segment 141 having one or more flow path(s) 339 for a fluid material to be released into digestive fluid 365 through dispenser 121 (when valve 320 is open). Valve 320 may actuate as a mechanical response to the fluid material exceeding a threshold pressure and/or as an electromechanical or other response to other information passing through the flow path(s) 339. Tether 137 may likewise include segment 142 to other dispensers and/or sense modules, optionally coupled via extensions of one or more of the flow paths 339 as shown. Segment 142 may optionally comprise optical fiber, for example, providing mechanical support for and an image data flow path from one or more lenses or other sensors.

With reference now to FIG. 4, shown is a variant that may serve as a context for introducing one or more processes and/or devices described herein. As shown system 400 may include an optional configuration of tether 137 terminating in a module comprising a cube-like unitary body 441 with six primary external surfaces 449 all bounded by a substantially convex external surface 448. The module may also include one or more instances of dispensers 443, fluidic access to at least some of which may be controlled by circuitry 447 as described herein. Circuitry 447 may, moreover, be configured to perform a variant of operation 220 (of FIG. 2) by generating a wireless signal confirming a bioactive material selection and dosage, such as by incorporating some or all features described below with reference to FIG. 13 or FIG. 15.

With reference now to FIG. 5, shown is a variant that may serve as a context for introducing one or more processes and/or devices described herein. As shown system 500 may include a unitary, substantially polyhedral body 551 with one or more convex external surfaces 558 and several other surfaces 559. System 500 may (optionally) include one or more instances of passive dispensers 553 each containing 1-15 grams of medicinal material configured to dissolve somewhat uniformly in a digestive tract over one or more days, weeks, or months. System 500 may likewise include one or more instances of dispensers 553, 554 and/or gaps 555 for accommodating various tether configurations as described herein.

With reference now to FIG. 6, shown is another variant that may serve as a context for introducing one or more processes and/or devices described herein. As shown system 600 may (optionally) comprise a unitary body having an overall average density smaller than 0.9 grams per milliliter and/or a cross-sectional diameter 662 larger than one millimeter. Alternatively or additionally, system 600 may include one or more passages 668 or other gaps collectively sufficient for receiving more than one tether or tether winding. System 600 may likewise include one or more instances of dispensers 663, 664, fluidic access to at least some of which may be controlled by circuitry 667 as described herein. This can occur, for example, in an embodiment in which respective segments 141, 142 of tether 137 (of FIG. 1) are tied or otherwise affixed to respective ends of system 600 and in which circuitry 667 activates dispenser 121 and otherwise performs flow 200 as described in one or more variants herein.

With reference now to FIG. 7, shown is an example of a system 700 immersed in digestive fluid 765. System 700 comprises several modules 701, 702, 703, 704 strung onto a single common tether 738 having an average diameter 797 less than 10% of length 796. The modules 701-704 may be held together by one or more capsules or bands 790 to facilitate ingestion. As shown, system 700 may (optionally) include one or more longest modules 703, 704 having a length 796 about 1-2 times that of an eyeball of the subject). For a typical human adult, for example, such a length 796 may be longer than 3 centimeters and/or less than 6 centimeters.

With reference now to FIG. 8, shown is an end view of system 700 (as viewed from the right, relative to FIG. 7). Each of modules 701-704 has roughly the same diameter 893 as one another, as shown, within a factor of 2. Alternatively or additionally, one or more of modules 701-704 may likewise have roughly the same length as length 796, within a factor of 2.

With reference now to FIG. 9, shown is an end view of system 700 (as viewed from the left, relative to FIG. 7). Unlike the view in FIG. 8, tether 738 appears roughly horizontal, stretched between respective tabs 991, 994. Each of modules 701-704 has one or more tabs 991, 994 at each end as shown.

With reference now to FIG. 10, shown is an example of a digestive tract interaction system 1000 comprising the modules 701-704 of FIGS. 7-9 in a fully expanded configuration. Tether 738 may be configured as a taut loop in this configuration, effectively coupling each pair of these modules 701-704 via a bore or other gap 1039 in each of the modules. In a variant in which one or more device(s) 1011, 1015 is configured to sever or otherwise release respective ends of tether 738 within gap 1039 of module 701, for example, the gaps 1039 of one or more other modules 702-704 are large enough to permit tether 738 to slip free so that all of the modules 701-704 may pass separately and safely per vias naturales. Such device(s) 1011, 1015 may (optionally) be configured to effect such a release in response to one or more of a temperature change indicating entry into a stomach, a pH increase of more than 2 points or some other indication of a sensed position, a remote control signal, an excessive tension in tether 738, or some other indication that system 1000 should or should not be fully expanded in a subject's current circumstances. Such device(s) 1011 may be configured to permit a clinical care provider to prevent or abort a deployment in the event that system 1000 has apparently begun to deploy in an esophagus or small intestine, for example.

For a typical human adult, a deployed diameter 1095 may be longer than 4 centimeters and/or less than 8 centimeters. As shown, modules 701-704 each has a nominal module length more than twice as long as its (respective) average cross-sectional diameter 893. At least one of the modules 703 may (optionally) have exactly one reservoir 1053. In some variants, each such reservoir 1052, 1053 may contain a respective therapeutic agent or a partial dosage of a common therapeutic agent. Alternatively or additionally, each such reservoir 1052, 1053 may be configured for dispensation under respectively different conditions. In some variants, for example, one or more other reservoirs 1051, 1054 may comprise a dispenser containing one or more of an antiviral or other antimicrobial agent, or some other component of a complex therapeutic regimen. In some variants, one or more such reservoirs 1051-1055 may comprise one or more of an anti-seizure medication, warfarin or other anticoagulant medications, insulin or other hormones, or other dosage-sensitive therapeutic agents.

To achieve the expanded configuration of system 1000 conveniently, at least some of tether 738 may (optionally) be constructed of a sufficiently elastic material able to be stretched by at least about 5-10% with negligible damage. Alternatively or additionally, some or all of tether 738 may be constructed to contract in an aqueous and/or acidic environment. Alternatively or additionally, one or more modules 701-704 may advantageously comprise an initially compressed body (especially as shown in FIG. 7), a body that swells in an aqueous and/or acidic environment, a shape memory element, and/or some other suitable uptake mechanism. Many such existing uptake mechanisms may be effectively implemented for this purpose (in device 1014, for example) without undue experimentation, as exemplified at FIG. 7 of U.S. patent application Ser. No. 11/975,371, titled ["Disintegrating Digestive Tract Interaction System," filed 17 Oct. 2007], also by Boyden et al. Such an active uptake mechanism may be triggered by a disengagement of band 790, a significant increase of ambient conductivity (and/or pressure or temperature, e.g.), or some other deployment-indicative condition. Other changes can occur as a mechanical or automatic response to such changes, such as a relaxation in crease 1034 causing port 1035 to open.

With reference now to FIG. 11, shown is a partial view 1050 of the expanded digestive tract interaction system 1000 of FIG. 10, magnified and in cross-section. Here it is apparent that module 701 comprises reservoir 1051 and a sleeve or other gap 1039 through which tether 738 passes. Module 704 likewise comprises reservoir 1054 and a sleeve or other gap 1039 through which tether 738 also passes. Tether 738 effectively couples module 701 with module 704 through gap 1039 as shown. Tether 738 also has a "middle portion" (in FIG. 10) configured to slip free from modules 702, 703 responsive to tether 738 dissolving, breaking, or otherwise decoupling module 701 from module 704.

To maintain an expanded configuration like system 100 in a gastric compartment, in some variants, each adjacent pair of modules may advantageously include a magnetic, adhesive, mechanical, or other latching feature such as tabs 991, 994 operable to extend into an adjacent module, for example. Such tabs 991, 994 may latch together (as shown in FIG. 11) or otherwise engage as respective faces 1129 thereof are drawn adjacent one another by tension in tether 738 (in response to immersion in fluid 765, for example). The protrusion 1198 of tab 991 into module 704 may (optionally) be about one millimeter or less, as shown. In some variants, moreover, such an engagement mechanism may release or relax in response to a slackening of tether 738. This can occur, for example, in a configuration in which tab 991 bears (upward as shown) against tether 738, optionally enough to release tab 994 in response to an absence of force (downward as shown) exerted by tether 738.

With reference now to FIG. 12, shown is a digestive tract portion and adjacent anatomical structures of a subject 1202 in a vicinity of which one or more technologies may be implemented. System 1200 may comprise one or more bodies 1240 respectively or collectively coupled with or via one or more tethers 1230 extending within or outside gastric compartment 170. In some variants, such tethers may extend downward (see FIG. 1) or upward into or through esophagus 1243. Tether 1230 may (optionally) extend to one or more dispensers 1221 and/or other modules 1225 in a vicinity of larynx 1245 or trachea 1247, for example, optionally permitting one or more therapeutic material dispensations 1229 (e.g. in pulmonary administrations via bronchi 1249). Such tethers may be supported by one or more dental prosthetheses 1215 via one or more supports 1217, or by simply being tied around a tooth. In some variants, support 1217 passes beside tongue 1216 and optionally into a side of the throat of subject 1202 with minimal interaction with the subject's soft palate. Alternatively or additionally, tether 1230 may be supported by being coated along its length with an anesthetic-infused adhesive, by being supported by a surgical staple or other implanted structure (e.g. at cricoid cartilage 1242), and/or by being fastened to one or more nasal stents or other such anatomical interface structures suitable for use in the present context. See, e.g., U.S. patent application Ser. No. 11/716,645 ("Orthonostric device and method of forming the same").

In some variants, system 1200 may include one or more signal or other flow path(s) 1231 through or along tethers as described herein. One or more such paths 1231, 1232 may extend to a sublingual dispenser 1226, for example, or to or from a location in the throat, nasal passage, intestine 180 (of FIG. 1), or other site in a vicinity of tract 101 and/or subject 1202. In some variants, for example, a signal flow path responsive to a nutrient level detected at sense module 122 may (optionally) travel up tether 137 to one or more modules in gastric chamber 170 implementing one or more of modules 110, 150 comprising body 1240, for example. Such detectable nutrients may comprise one or more instances of proteins, fats, vitamins, minerals, trace elements, carbohydrates, or substantially any ratio or other combination thereof. Such detection may comprise a determination whether one or more measurements indicative of one or more such nutrients (or a determinant derived from them) are within a nominal range derived from empirical data, for example, or at a lower-than-nominal level or a non-ideal level.

Such signal flow may then undergo a programmatic aggregation or delay and/or change form (from optical or electrical to a pressure or other mechanical manifestation, for example) before triggering dispensation via one or more dispensers 121, 1221, 1226 optionally provided in systems 100, 1200 described herein. In some variants, moreover, such dispensation may be administered to other sites, such as by routing a small flow tube into a blood vessel or other location in the abdominal cavity through an incision in the esophagus.

In some variants, body 1240 may have an annular configuration of a general type exemplified by those of FIG. 1 or 7-12 or of U.S. Pat. No. 4,758,436 ("Drug delivery device which may be retained in the stomach for a controlled period of time"). Alternatively or additionally, body 1240 may have attributes of one or more other instances of modules 1250, 1260, 1280, 1290 described next.

In an instance in which body 1240 includes one or more attributes of module 1250, for example, body 1240 may comprise a single reservoir 1254 and/or a single-reservoir port 1251 for dispensing one or more therapeutic materials as described herein. Module 1256 further comprises a bladder or other such lower-density internal structure so that module 1250 is at least somewhat buoyant relative to fluid 1255 as shown.

In an instance in which body 1240 includes one or more attributes of module 1260, for example, body 1240 may comprise a primary reservoir 1264 and one or more other reservoirs 1268 in respective chambers of a common container 1269, optionally having higher-than-ambient pressure (by at least 1%, for example, in absolute terms). In a variant in which primary reservoir 1264 contains one or more bioactive agents, reservoir 1268 may comprise a carrier, for example, or a pressure-maintaining reservoir. In some contexts it may be preferable that container 1269 itself have a density larger than 1.1 g/ml. This may permit reservoir 1268 to contain a gaseous component for example, even without bringing the overall density of module 1260 below 0.8 g/ml. Alternatively or additionally, module 1260 may adjoin one or more conduits or other ports 1261 configured for permitting a valve elsewhere to release bioactive substances therein.

In an instance in which body 1240 includes one or more attributes of module 1280, for example, body 1240 may comprise a reservoir 1284 with an irregular outer surface and/or one or more gaps 1283, actuators, or other features for facilitating a change in a configuration thereof in situ. To further understand the operation of such features, see, e.g., U.S. patent application Ser. No. 11/702,888 ("Gastro-intestinal device and method for treating addiction") or U.S. Pat. No. 6,994,095 ("Pyloric valve corking device and method"). By drawing tether 1281 through gap 1283 with a catheter or other manipulation device, for example, pressure one on or more fluids inside reservoir 1284 may be increased in situ.

In an instance in which body 1240 includes one or more attributes of module 1290, for example, body 1240 may comprise a plurality of reservoirs 1294, 1296 having respectively different therapeutic substances therein, one or more of which may be directly releasable through their openings 1298. Tether 1291 may likewise include flow paths in either direction (for inflating or dispensing from reservoir 1294, for example, or for bearing electrical signals in either or both directions). Module 1290 may, in particular, combine two or more respective features of reservoir-containing modules 1250, 1260, 1280 described above, in each of the (component) reservoirs 1294, 1296, 1297 shown. In some variants, moreover, one or more such reservoirs 1297 is configured for selective release as exemplified in relation to FIG. 13.

With reference now to FIG. 13, shown is system 1300 for use in or with body 1310 immersed adjacent fluid 1305 in which one or more technologies may be implemented. System 1300 may comprise one or more instances of instruction sequences 1316, measurement data 1318 and/or other logic 1330, some or all of which may reside in static or dynamic memory 1320. Such logic 1330 may comprise one or more instances of decision modules 1321, 1322, 1323 or other control modules 1324; timing logic 1325; measurement-responsive logic 1326; configuration modules 1327; or other logic units 1328, 1329. Alternatively or additionally, system 1300 may comprise one or more instances of glucose sensors 1341, inhalation detectors 1342, in situ sense modules, or other sensor modules 1340 as described herein. These and other components of system 1300 may be configured to bear one or more instances of identifiers 1351, 1352 or indications 1361, 1362, such as one or more antennas 1380 or processors 1390 optionally provided therein. In addition to one or more instances of system 1300, body 1310 may comprise one or more ports or other continuous dispensers 1301 (or one or more releasable capsules or other discrete dispensers 1302) configured for dispensing from a bioactive material supply 1307. Body 1310 may likewise comprise one or more ports or other continuous dispensers 1303 (or one or more releasable capsules or other discrete dispensers 1304) configured for dispensing from at least one other bioactive-material-containing supply 1308. As shown, one or more processors may implement a bioactive material selection directly or indirectly, in respective embodiments, by selectively outputting one or more actuator driver outputs 1391, 1392, 1393, 1394 respectively operable for initiating or otherwise controlling dispensation from dispensers 1301-1304 as shown.

In some variants, system 1300 is configured for performing one or more variants of flow 200 (of FIG. 2) described herein. In an embodiment in which antenna 1380 is configured to perform operation 220, for example, antenna 1380 may likewise receive a wireless signal (as signal 1350) indicative of one or more ports, supplies, or other dispensers inside tract 101, for example. In response, one or more decisions module 1321-1323 may (optionally) be configured to signal a decision of which actuator or other dispenser control of a module to activate in response to a received wireless signal. This may result in a performance of operation 210 (by administering the one or more selected dosages, for example) and/or of operation 220 (by transmitting one or more wireless signals) within a digestive tract.

With reference now to FIG. 14, shown is an implantable or ingestible system 1400 suitable for exposure to digestive or other bodily fluid 1465 in which one or more technologies may be implemented. System 1400 may comprise two or more reservoirs 1492, 1493, 1494, 1495, 1496, 1497 operating in a cooperative fashion according to an a priori regimen and/or sensor input or other signals 1441. Such signals may originate from a remote care provider or other external module 1440, for example, optionally after being received locally via a wireless medium. External module 1440 may comprise a wireless router, a radio-frequency identification (RFID) device, and/or a handheld device, for example. Alternatively or additionally, external module 1440 may comprise an article configured to function while worn by a subject, such as a belt or prosthetic device.

One or more such reservoirs 1492-1497 may be configured to separate from the others for dispensation during passage per vias naturales in some embodiments. Alternatively or additionally, one or more others may be configured for selective dispensation via one or more ports 1401, 1402 to respective flow paths as described herein, for example. Such flow paths may pass into an esophagus and/or an intestine, for example, as variously described herein.

As shown, reservoir 1492 may comprise one or more instances of hormones 1417 or other bioactive ingredients and/or carrier materials 1418. Reservoir 1493 may likewise comprise many doses 1432 of a bioactive powder, propellant, or other flowable material. Reservoir 1494 may comprise one or more instances of antimicrobial agents 1473 and/or other bioactive ingredients optionally comprising carrier materials 1478. Reservoir 1497 may comprise a selectable concentration or other mode of dosage 1445, optionally with one or more other instances of ingredients 1451 or other markers 1456. System 1400 may further comprise one or more other compositions 1483, 1484, one or more of which may comprise one or more instances of alkaline materials 1485 or other materials useful for adjusting pH. Optionally some or all such reservoirs may be housed within one or more capsules 1409, optionally at a stable, higher-than-ambient pressure and near-neutral buoyancy. In other variants, however, creases or other hinging structures may be used for coupling respective ones of reservoirs 1492-1497 into one or more ring-like, H-shaped, tetrahedral, or other expanded forms useful for "loitering" for more than a day in a gastric chamber, for example, as described herein.

With reference now to FIG. 15, shown is a system in which one or more technologies may be implemented comprising one or more modules 1500 optionally operable for communication with one or more user interfaces 1510 operable for relaying user output 1516 and/or input 1518. Module 1500 comprises one or more instances of (electrical, electromechanical, software-implemented, firmware-implemented, or other control) devices 1520. Device 1520 may comprise one or more instances of memory 1530; processors 1540; ports 1545, 1546; valves 1551, 1552; antennas 1557; power or other supplies 1558; logic modules 1561, 1562, 1563 or other signaling modules 1560; gauges 1578 or other such active or passive detection components 1570; or piezoelectric transducers 1582, shape memory elements 1583, micro-electromechanical system (MEMS) elements 1584, or other actuators 1580. Such detection components 1570 may comprise one or more instances of sensors 1571 operable for measuring or otherwise detecting a higher-than-nominal concentration of alcohol or other controlled substances, sensors 1572 operable for accepting an indication of or otherwise responding to a proximity to an artificial device from within a portion of the digestive tract, sensors 1573 for measuring or otherwise detecting a higher-than-nominal concentration of an artificial control marker, sensors 1574 operable for measuring or otherwise detecting a higher-than-nominal concentration of lipids, sensors 1575 operable for accepting an indication of or otherwise responding to a pH or other environmental attribute, sensors 1576 operable for measuring or otherwise detecting a higher-than-nominal concentration of carbohydrates or other nutrients, or sensors 1577 operable for accepting an indication of or otherwise responding to a departure of one or more artificial devices from within a specific portion of the digestive tract. Many such devices may be implemented in software or otherwise in memory 1530, such as one or more executable instruction sequences 1532 or supplemental information 1535 as described herein. Alternatively or additionally, in various embodiments, any such devices 1520 may likewise (optionally) handle one or more instances of quantities 1591, 1592; one or more identifiers 1593 or other indications 1594; or other components of messages 1595 or other values 1596, 1597, 1598, 1599 as described herein.

Referring again to FIGS. 12-14, those skilled in the art will appreciate that component modules 1296, 1297 or other "modules" described herein may implement one or more reservoirs 1492-1497 and/or one or more described attributes of body 1310, as described above. Any such module may likewise implement one or more devices 1520, logic 1310, or other attributes of an electrical or other system as described below. In light of teachings herein, numerous existing techniques may be applied for forming or assembling components of modules suitable for use in various portions of a digestive tract for various functions as described herein without undue experimentation. See, e.g., U.S. Pat. No. 7,182,957 ("Polymer blends that swell in an acidic environment and deswell in a basic environment"); U.S. Pat. No. 7,097,851 ("Oral formulation for gastrointestinal drug delivery"); U.S. Pat. No. 7,041,083 ("Medical catheter assembly including a removable inner sleeve and method of using the same"); U.S. Pat. No. 6,797,283 ("Gastric retention dosage form having multiple layers"); U.S. Pat. No. 6,120,803 ("Prolonged release active agent dosage form adapted for gastric retention"); U.S. Pat. No. 5,198,229 ("Self-retaining gastrointestinal delivery device"); U.S. Pat. No. 4,522,625 ("Drug dispenser comprising wall formed of semipermeable member and enteric member"); U.S. Pat. Pub. No. 2007/0178160 ("Gastro-intestinal device and method for treating addiction"); U.S. Pat. Pub. No. 2007/0106213 ("Gastrointestinal applicator and method of using same"); U.S. Pat. Pub. No. 2006/0068003 ("System for increasing compliance with medication regime"); U.S. Pat. Pub. No. 2005/0249799 ("Polymeric drug delivery system for hydrophobic drugs"); U.S. Pat. Pub. No. 2005/0201974 ("Bioadhesive polymers with catechol functionality"); U.S. Pat. Pub. No. 2005/0058701 ("Active drug delivery in the gastrointestinal tract"); U.S. Pat. Pub. No. 2004/0224019 ("Oral controlled release system for targeted drug delivery into the cell and its nucleus for gene therapy, DNA vaccination, and administration of gene based drugs"); U.S. Pat. Pub. No. 2004/0109894 ("pH triggered targeted controlled release systems for the delivery of pharmaceutical active ingredients"); U.S. Pat. Pub. No. 2003/0232078 ("Formulation & dosage form for the controlled delivery of therapeutic agents"); U.S. Pat. Pub. No. 2003/0113371 ("Composition and method for maintaining blood glucose level by employing the hydrophilic matrix based oral controlled release antidiabetic composition"). Those skilled in the art will also recognize how to apply numerous existing techniques for taking provisional, alternate, overlapping, or completion actions relating to such decisions as exemplified herein without undue experimentation, in light of these teachings. Such variations may be typically be implemented with existing manufacturing techniques in light of these teachings.

In some variants in which module 1500 implements system 1300, system 1300 may comprise one or more ports 1545 or other components operable for interaction with processor 1390 or other circuitry for implementing a bioactive material selection from within a digestive tract as described herein, including one or more valves 1551 configured to operate within gastric compartment 170. Alternatively or additionally, system 1300 may likewise be configured to include or otherwise communicate with one or more other valves 320 (of FIG. 3), 1552 or dispensers 1221 configured to operate outside gastric compartment 170. In some variants, for example, one or more dispensers 1304 may be configured to release one or more fluid antibiotics or the like continuously from supply 1308 into a subject's intestine, once triggered by processor 1390 (e.g. by actuator driver output 1394).

Figure 16:
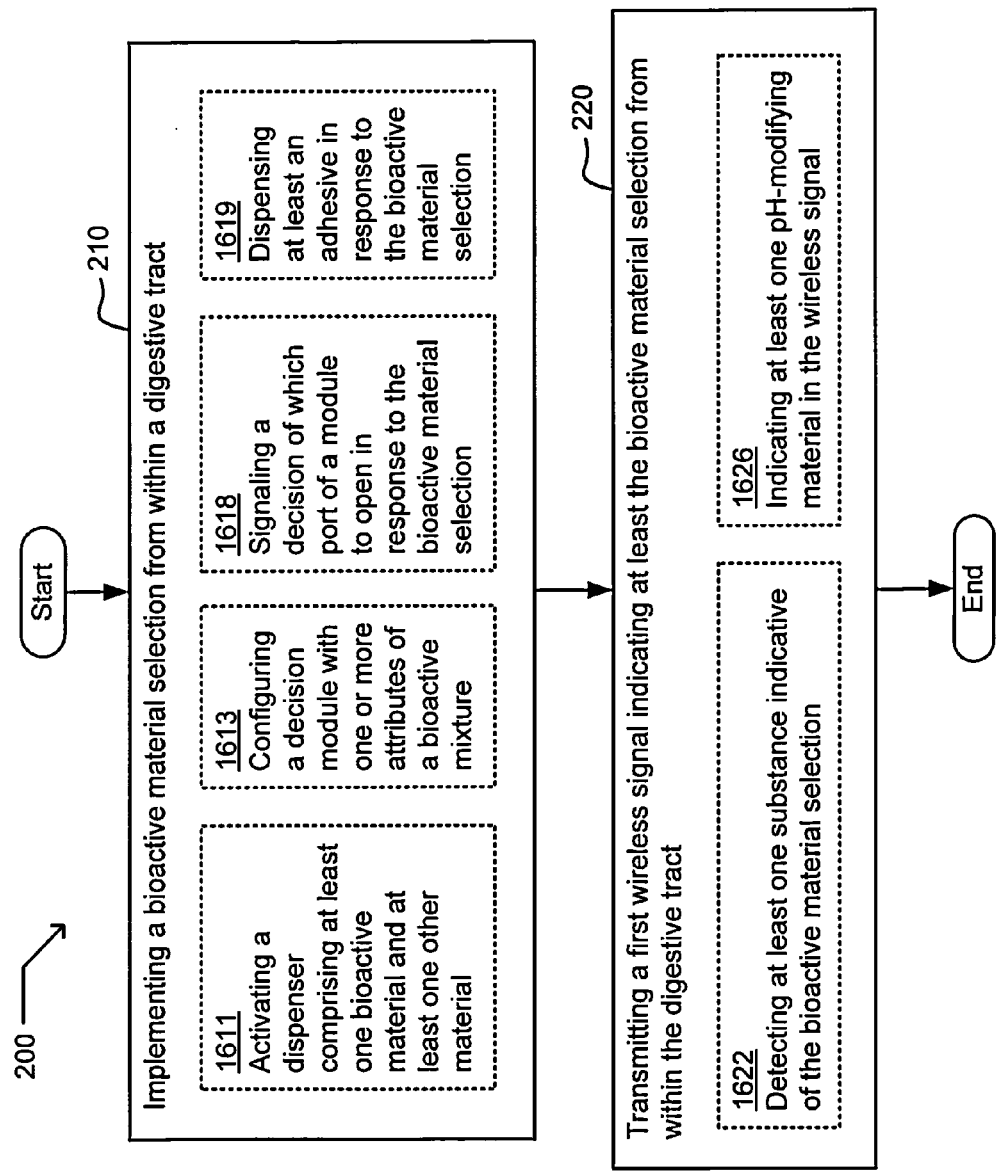
FIGS. 16-17 depict variants of the flow of FIG. 2.

With reference now to FIG. 16, there are shown several variants of the flow 200 of FIG. 2. Operation 210—implementing a bioactive material selection from within a digestive tract—may (optionally) include one or more of the following operations: 1611, 1613, 1618, or 1619. In some embodiments, variants of operation 210 may be performed by one or more instances of special-purpose instructions or other logic 1330, processor 1390, or other device(s) effectively implementing logic operable for signaling deployments, dispensations or other actions described herein, such as via one or more configurable ports, nozzles, pumps, valves or other actuators 1580 or actuator driver outputs 1391-1394, or other control features as described herein. Operation 220—transmitting a first wireless signal indicating at least the bioactive material selection from within the digestive tract—may include one or more of the following operations: 1622 or 1626. In some embodiments, variants of operation 220 may be performed by one or more instances of sense modules comprising sensors and/or other components 1570 and/or signaling modules 1560, antennas, processors, or other such communication logic as described herein.

Operation 1611 describes activating a dispenser comprising at least one bioactive material and at least one other material (e.g. processor 1390 triggering one or more actuator driver outputs 1392, 1393 selectively to release or otherwise activate one or more dispensers 1302, 1303 each including a polymer or other carrier material 1478 with acyclovir or another antimicrobial agent 1473 via a respective actuator driver output 1392, 1393). Such polymer-containing materials may (optionally) include a water soluble polymer component selected from the group consisting of soluble cellulosic materials, ethylene vinyl alcohol, ethylene maleic anhydride copolymer, polyacrylates, polycaprolactones, polyanhydrides, poly(ortho)esters, biodegradable polyurethanes, polyactones, polyamides and polypeptides, gelatin and derivatives, polyacrylonitriles, polyesters, and combinations thereof.

Operation 1611 can occur, for example, in a context in which dispenser 1302 is implemented as a port; in which dispenser 1303 is implemented as a releasable capsule; and in which supplies 1307, 1308 are composite materials with at least one bioactive ingredient. In some variants, for example, a carrier material implements a coating that at least partly limits contact between the antimicrobial agent 1473 and digestive fluid 1305, 1465 until antimicrobial agent 1473 enters a desired portion of a small intestine. Alternatively or additionally, the "other" material may include one or more of croscarmellose sodium, povidone, microcrystalline cellulose, calcium carbonate, calcium phosphate, various sugars, starches, cellulose derivatives, gelatin, pregelatinized starch, polymers, or substantially any combination thereof. Such carrier materials may comprise and/or contain such "other" materials, moreover, in substantially any combination.

In light of these teachings, numerous existing techniques may be applied for constructing capsules or other ingestible or releasable structures as described herein without undue experimentation. See, e.g., U.S. Pat. No. 7,182,959 ("Rapidly dissolving dosage form and process for making same"); U.S. Pat. No. 6,962,715 ("Method and dosage form for dispensing a bioactive substance"); U.S. Pat. No. 6,960,356 ("Orally administered drug delivery system providing temporal and spatial control"); U.S. Pat. No. 6,929,636 ("Internal drug dispenser capsule medical device"); U.S. Pat. No. 6,936,279 ("Microcrystalline zeaxanthin with high bioavailability in oily carrier formulations"); U.S. Pat. No. 6,866,863 ("Ingestibles possessing intrinsic color change"); U.S. Pat. No. 6,767,567 ("Ingestible elements"); U.S. Pat. No. 6,703,013 ("Polystyrene sulfonate-containing gel preparation"); U.S. Pat. No. 6,677,313 ("Method for gene therapy using nucleic acid loaded polymeric microparticles"); U.S. Pat. No. 6,475,521 ("Biphasic controlled release delivery system for high solubility pharmaceuticals and method"); U.S. Pat. No. 6,638,533 ("Pulse dosage formulations of methylphenidate and method to prepare same"). Those skilled in the art will also recognize how to apply numerous existing techniques for taking provisional, alternate, overlapping, or completion actions relating to such applications as exemplified herein without undue experimentation, in light of these teachings. Substantially any of these structures or techniques may be used in some form for constructing modules, flow paths, dispensers, or other feature described herein without undue experimentation.

Operation 1613 describes configuring a decision module with one or more attributes of a bioactive mixture (e.g. processor 1390 invoking configuration module 1327 or other logic 1330 for configuring decision module 1323 with measurement-responsive logic 1326 and/or timing logic 1325). Measurement-responsive logic 1326 may be configured to trigger an administration of insulin via dispensation 1229 into larynx 1245, for example, in response to detection of a lower-than-nominal blood glucose level and to apparent inhalation. This can occur, for example, in an embodiment in which module 1225 comprises one or more inhalation detectors 1342 and a suitably-positioned blood glucose sensor 1341 or the like (optionally accessible to external module 140, in some cases). Alternatively or additionally, timing logic 1325 may be configured to trigger an administration of one or more dosages 1445, 1451 (of a pain reliever, for example) at regular or other programmatic intervals.

Operation 1618 describes signaling a decision of which port of a module to open in response to the bioactive material selection (e.g. one or more decision modules 1322, 1323 each causing one or more respective ports of modules 1294, 1296 to open, such as by actuating microfluidic pumps or valves thereof). This can occur, for example, in embodiments in which module 1290 incorporates one or more instances of system 1300, in which decision module 1322 controls such dispensation via module 1294 to implement a hormone-dispensing reservoir, in which decision module 1323 controls dispensation via module 1296, and in which logic 1330 performs operation 210. In some variants, for example, decision modules may always implement a received or a priori drug administration protocol except when a detectable condition warrants a delay: a pH measurement in a vicinity of the dispenser being below a threshold, a subject currently exhaling, a gastric chamber having one or more measurements indicative of undigested sugar, or when sensor module 1340 is able to detect other such conditions. In some variants, for example, sensor module 1340 may incorporate one or more sensors 1571-1577 or other such components 1570 as described above. Alternatively or additionally, some such decision modules 1322 may cause one or more ports 1402 or other dispensers 1301 to open or close to an intermediate degree under closed-loop control. In a variant in which module 110 (of FIG. 1) implements system 1300 in capsule 1409 (of FIG. 14), for example, decision module 1322 may be configured as a negative-feedback control loop maintaining hormone 1417 dispensed via port 1402 within a nominal range as detected at sense module 122. In some variants, operation 220 may likewise include indicating a detected or controlled level at regular intervals, for example, or in response to each such detected or caused change.

Operation 1619 describes (e.g. module 1290 severing a coupling or otherwise selectively releasing one or more component modules 1294, 1296 or other unitary structures coated with bioadhesive material). This can occur, for example, in embodiments incorporating a preparatory phase of coating or otherwise combining one or more selected bioactive materials with a suitable binding agent. Alternatively or additionally, in some variants, one or more decision modules 1321 may select from two or more bioactive, adhesive-containing compositions 1483, 1484 as a material selection made in preparation for other phases of operation 210.

In light of these teachings, numerous existing techniques may be applied for using biologically compatible binding agents as described herein without undue experimentation. See, e.g., U.S. Pat. No. 7,265,098 ("Polyacid/polyalkylene oxide gels and methods for their delivery"); U.S. Pat. No. 7,255,874 ("Biocompatible polymers and adhesives: compositions, methods of making and uses related thereto"); U.S. Pat. No. 7,097,851 ("Oral formulation for gastrointestinal drug delivery"); "); U.S. Pat. No. 7,056,550 ("Medical devices, drug coatings and methods for maintaining the drug coatings thereon"); U.S. Pat. No. 6,800,296 ("Modification of surfaces using biological recognition events"); U.S. Pat. No. 6,764,696 ("Effervescent drug delivery system for oral administration"); U.S. Pat. No. 6,689,380 ("Remote and local controlled delivery of pharmaceutical compounds using electromagnetic energy"); U.S. Pat. No. 6,582,720 ("Medicinal compositions adhering to stomach/duodenum"); "); U.S. Pat. No. 6,576,712 ("Preparation of hydrophilic pressure sensitive adhesives having optimized adhesive properties"); U.S. Pat. No. 6,428,813 ("Gastrointestinal mucosa-adherent pharmaceutical composition"). Those skilled in the art will also recognize how to apply numerous existing techniques for taking provisional, alternate, overlapping, or completion actions relating to such applications as exemplified herein without undue experimentation, in light of these teachings. Binding agents may likewise be used for coupling modules as described herein, before or during deployment.

Operation 1622 describes detecting at least one substance indicative of the bioactive material selection (e.g. sense module 122 detecting one or more marker materials indicative of dispenser 151 being active). This can occur, for example, in embodiments in which dispenser 151 includes a reservoir having one or more drugs mixed with higher-than-nominal levels of colorants, uncommon minerals, inert materials, or other readily-detectable materials of suitably low toxicity, and in which sense module 122 may detect such materials. Alternatively or additionally, in some contexts, sense module 122 may implement one or more targeted assays or other sensors configured to detect drugs or other bioactive ingredients 1451 (inferentially via artificial markers 1456, metabolytes, or other markers thereof, for example).

In light of these teachings, numerous existing techniques may be applied for using artificial markers or other diagnostically useful indicator materials as described herein without undue experimentation. See, e.g., U.S. Pat. No. 7,256,398 ("Security markers for determining composition of a medium"); U.S. Pat. No. 7,252,932 ("Methods for the detection, analysis and isolation of nascent proteins"); U.S. Pat. No. 7,238,471 ("Method of diagnosing, monitoring, staging, imaging and treating breast cancer"); U.S. Pat. No. 7,228,159 ("Optical sensor containing particles for in situ measurement of analytes"); U.S. Pat. No. 7,202,045 ("Detection and treatment of cancers of the lung"); U.S. Pat. No. 7,198,756 ("Non-invasive measurement of pH"); U.S. Pat. No. 7,118,919 ("13 C glucose breath test for the diagnosis of diabetic indications and monitoring glycemic control"); U.S. Pat. No. 7,118,912 ("Methods and compositions for categorizing patients"); U.S. Pat. No. 7,105,300 ("Sequencing by incorporation")"); U.S. Pat. No. 7,070,937 ("Marker useful for detection and measurement of free radical damage and method"); U.S. Pat. No. 6,977,068 ("Method for detection of fibrin clots"); U.S. Pat. No. 6,905,884 ("Fluorescent cobalamins and uses thereof"); U.S. Pat. No. 6,703,045 ("Composition and method for maintaining blood glucose level"); U.S. Pat. No. 6,753,135 ("Biological markers for evaluating therapeutic treatment of inflammatory and autoimmune disorders"); U.S. Pat. No. 6,680,172 ("Treatments and markers for cancers of the central nervous system"); U.S. Pat. No. 6,628,982 ("Internal marker device for identification of biological substances"); U.S. Pat. No. 6,585,646 ("Screening test and procedure using skin patches"); U.S. Pat. No. 6,534,323 ("Compositions and methods for early detection of heart disease"); U.S. Pat. No. 6,500,625 ("Methods for diagnosing cancer or precancer based upon hnRNP protein expression"); U.S. Pat. No. 6,419,896 ("Non-invasive approach for assessing tumors in living animals"); U.S. Pat. No. 5,639,656 ("Antibodies reactive with biological markers of benign prostate hyperplasia"). Those skilled in the art will also recognize how to apply numerous existing techniques for taking provisional, alternate, overlapping, or completion actions relating to such applications as exemplified herein without undue experimentation, in light of these teachings. One or more ports 1545, 1546, valves 1551, 1552, pumps, or other actuators may likewise be used for selecting among two or more bioactive mixtures or other materials, one or more of which may include such marking ingredients.

Operation 1626 describes indicating at least one pH-modifying material in the first wireless signal (e.g. control module 162 signaling a dispensation of a proton inhibitor or alkaline material 1485). This can occur, for example, in a context in which control module 162 directs, detects, or otherwise infers a dispensation of such material via dispenser 161, alone or in combination with one or more excipients or other carriers. Alternatively or additionally, a wireless signal 139 bearing one or more such indications may likewise include a port identifier, one or more dosage or other concentration-indicative values, a time interval or other indication of remaining materials in dispenser 161, a record of one or more pH measurements, or other such supplemental information 1535.

In light of these teachings, numerous existing techniques may be applied for directly or indirectly affecting a pH of a local portion of a digestive tract as described herein without undue experimentation. See, e.g., U.S. Pat. No. 7,276,252 ("Method and form of a drug delivery device, such as encapsulating a toxic core within a non-toxic region in an oral dosage form"); U.S. Pat. No. 7,144,877 ("Bile-acid derived compounds for enhancing oral absorption and systemic bioavailability of drugs"); U.S. Pat. No. 7,101,567 ("Controlled release preparations having multi-layer structure"); U.S. Pat. No. 6,926,909 ("Chrono delivery formulations and method of use thereof"); U.S. Pat. No. 6,875,793 ("Once-a-day controlled release sulfonylurea formulation"); U.S. Pat. No. 6,797,268 ("Pharmaceutical composition useful in the treatment of peptic ulcers"); U.S. Pat. No. 6,730,327 ("Polymer blends that swell in an acidic environment and deswell in a basic environment"); U.S. Pat. No. 6,726,924 ("Oral liposomal delivery system"); U.S. Pat. No. 6,764,696 ("Effervescent drug delivery system for oral administration"); U.S. Pat. No. 6,692,771 ("Emulsions as solid dosage forms for oral administration"); U.S. Pat. No. 6,600,950 ("Iontophoretic treatment system"). Those skilled in the art will also recognize how to apply numerous existing techniques for taking provisional, alternate, overlapping, or completion actions relating to such applications as exemplified herein without undue experimentation, in light of these teachings. In some variants, one or more reservoirs 554, 664, 1054 or the like described herein may comprise a pH-reducing or pH-increasing component in a liquid form, for example, optionally configured for release directly into gastric compartment 170. Alternatively or additionally, such dispensation may be controlled or otherwise informed by one or more sensors 1575 or other components 1570 operable for detecting a pH, a pH change, or one or more other environmental circumstances as designated by a physician or other medical or veterinary professional.

Figure 17:
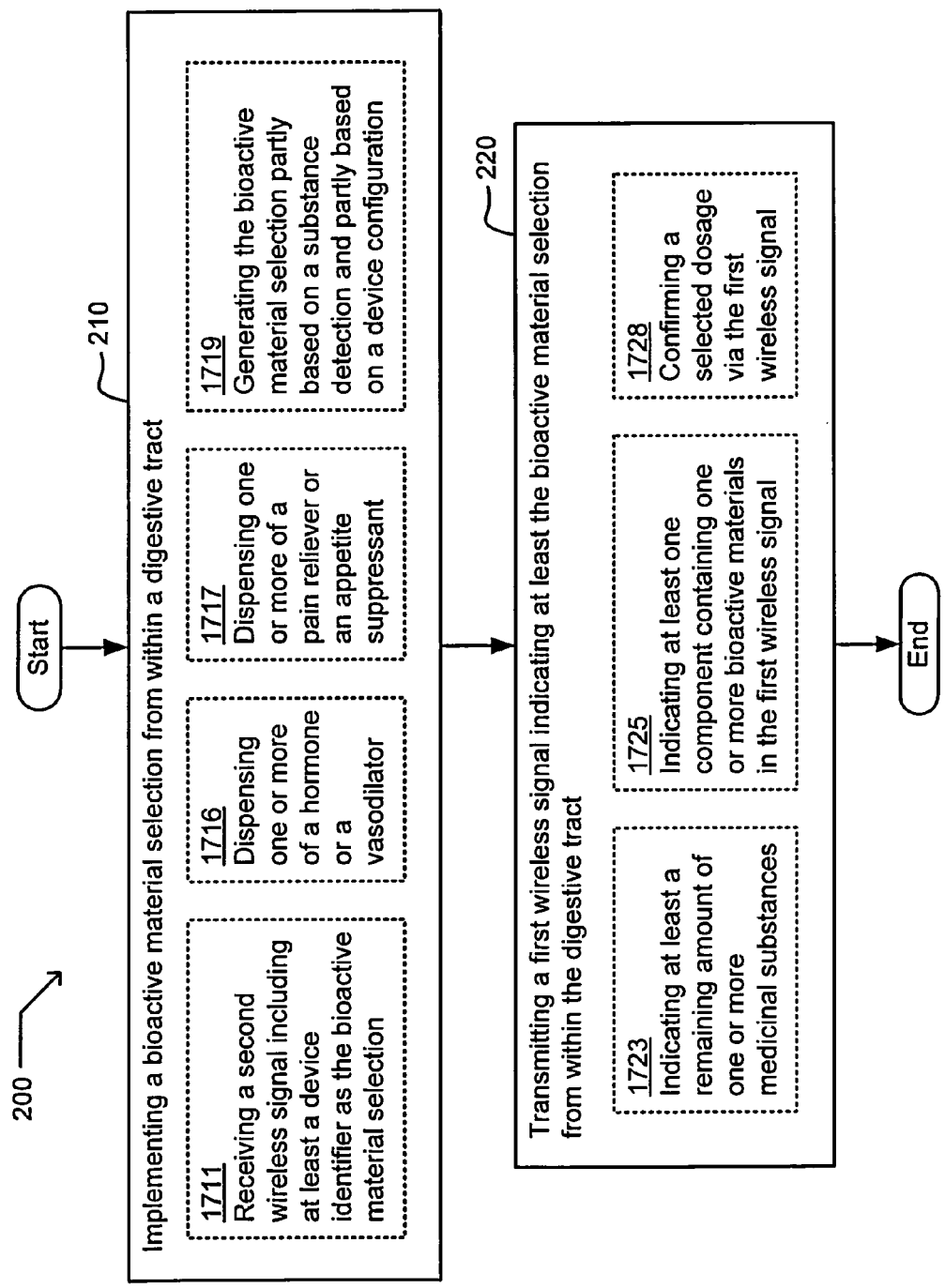

With reference now to FIG. 17, there are shown several variants of the flow 200 of FIG. 2 or FIG. 16. Operation 210—implementing a bioactive material selection from within a digestive tract—may (optionally) include one or more of the following operations: 1711, 1716, 1717, or 1719. In light of teachings herein, numerous existing techniques may be applied for acquiring or using measurements or other detectable phenomena relating to a digestive tract for various functions as described herein without undue experimentation. See, e.g., U.S. Pat. No. 7,217,245 ("Noninvasive methods for detecting abnormalities in a subject such as disease or dysfunction"); U.S. Pat. No. 7,160,731 ("Examination method of buffer capacity of saliva and examination instrument of buffer capacity of saliva"); U.S. Pat. No. 7,155,269 ("Stress evaluation apparatus"); U.S. Pat. No. 7,062,306 ("Spectroscopy illuminator with improved delivery efficiency for high optical density and reduced thermal load"); U.S. Pat. No. 6,365,128 ("Monitoring gastrointestinal function to guide care of high risk patients"); U.S. Pat. No. 6,264,611 ("Monitor for interventional procedures"); U.S. Pat. No. 6,258,046 ("Method and device for assessing perfusion failure in a patient by measurement of blood flow"); U.S. Pat. No. 6,125,293 ("Method for determining the pH in the mucosa of the stomach or the gastrointestinal tract"); U.S. Pat. No. 5,833,625 ("Ambulatory reflux monitoring system"); U.S. Pat. No. 5,263,485 ("Combination esophageal catheter for the measurement of atrial pressure"). Those skilled in the art will also recognize how to apply numerous existing techniques for taking provisional, alternate, overlapping, or completion actions relating to such decisions as exemplified herein without undue experimentation, in light of these teachings. Such variations may be implemented in instruction sequence 1532 or other implementations of special-purpose logic implementing one or more functions described herein. In some variants operation 210 may be performed, for example, by elements individually and collectively implementing a current decision about which of several bioactive materials to dispense into the digestive tract.

Operation 1711 describes receiving a second wireless signal including at least a device identifier as the bioactive material selection (e.g. antenna 1557 receiving identifier 1351 of a port, actuator, module, valve, reservoir, or other device 1520 within wireless signal 139). This may be detected, for example, by logic unit 1329 being operable to receive some portion or other indication 1594 of wireless signal 139 sufficient to determine whether one or more such identifiers 1351, 1352 may be recognized therein.

Operation 1716 describes dispensing one or more of a hormone or a vasodilator (e.g. one or more dispensers 1221, 1304 releasing one or more hormones 1417 and/or other components into an appropriate absorptions site of subject 1202 according to a daily or more frequent regimen). This can occur, for example, in embodiments in which a corticosteroid or other hormone in fluid form is dispensed steadily via a conduit or other port exiting a reservoir into a gastric compartment (like those shown in FIGS. 12-14, for example) or the intestines. Alternatively or additionally, one or more dispensers 1221, 1226 may be configured to dispense an alpha blocker, a corticosteroid, a nitric oxide source, or other such materials. Nozzles or other such dispensers 1221 may, moreover, propel one or more dispensations 1229 in mist or powder form for rapid absorption via the lungs.

Operation 1717 describes dispensing one or more of a pain reliever or an appetite suppressant (e.g. one or more dispensers 1226, 1301 injecting a metered dose of a pain reliever). This can occur, for example, in a context in which one or more reservoirs 1493 are assigned to dispense into a specific dose 1432 into a mouth, larynx, small intestine, or other mucous membrane portion at daily or more frequent intervals. Alternatively or additionally, a dosage for a specific individual may be continuously administered and/or modulated by diluting the pain reliever or a muscle relaxant with a carrier material or the like. In some cases, dispenser 1302 may likewise be configured to release capsules or other releasable dispensers 1302, 1304 into digestive fluid 1305.

Operation 1719 describes generating the bioactive material selection partly based on a substance detection and partly based on a device configuration (e.g. logic unit 1328 selecting medicinal composition 1483 in response to a signal 1441 from external module 1440 or to measurement data 1318 from a proximity of a digestive tract as described herein). This can occur, for example, in a context in which sensor module 1340 detects a recognizable condition in such data (e.g. in response to a concentration of an analyte crossing a threshold maximum or minimum).

Operation 220—transmitting a first wireless signal indicating at least the bioactive material selection from within the digestive tract—may optionally be performed by elements individually and collectively indicating a recent or current implementation of the decision via the wireless signal(s). In some variants of FIG. 17, for example, operation 220 may include one or more of the following operations: 1723, 1725, or 1728. Operation 1723 describes indicating at least a remaining amount of one or more medicinal substances (e.g. gauge 1578 expressing a percentage or other quantity 1591, 1592 indicative of an apparent amount of a therapeutic material dosage 1445 remaining in one or more reservoirs 1496, 1497). Such a quantity 1591 may be expressed in units of time used or remaining, in milliliters or other physical dimensions, and/or in terms of an active ingredient or other useful quantitative determinant. Such quantities 1591, 1592 may trigger or otherwise affect a message in the wireless signal, for example, such as by providing a warning that a supply of a hormone or other extended-duration medication is imminently or recently exhausted.

Operation 1725 describes indicating at least one component containing one or more bioactive materials in the first wireless signal (e.g. signaling module 1560 invoking logic module 1561 for generating a message or other value 1596 confirming that module 701 is present and/or deployed). This can occur, for example, in an embodiment in which ring-type module 150 implements module 1500, in which signaling module 1560 performs operation 220, in which wireless signal 139 includes one or more values 1599 as described herein, and in which one or more actuators 1580 have opened one or more ports 1545 exposing a reservoir or other supply to fluid in gastric compartment 170. In a variant in which ring-type module 150 implements one or more systems 1000, 1400 described above, for example, one or more instances of ports 1035, 1401 may be positioned in a crease 1034 or other structure that opens as a direct mechanical response to system deployment.

Operation 1728 describes confirming a selected dosage via the first wireless signal (e.g. signaling module 1560 invoking logic module 1563 for generating a message portion or other value 1597 including "20 mg" or dosage "B" for use in generating wireless signal 139). This can occur, for example, in embodiments in which module 110 includes an implementation of system 1300, in which the bioactive material selection accompanies a request or other transmission, and in which signaling module 1560 performs operation 220. Alternatively or additionally, one or more modules 1284, 1294 of body 1240 may likewise include such an implementation of system 1300 operable for performing operation 1728 and/or other optional operations as described herein.

In some variants combining features described above, antenna 1557 (of FIG. 15) may perform operation 1711—receiving a second wireless signal including at least a device identifier as the bioactive material selection—in a context in which the "second" wireless signal includes information effectively identifying a bioactive material. Such identifiers may explicitly refer to one or more formulations of insulin, an osteocalcin, a thiazolidinione or other anti-inflammatory materials, incretin or other hormones, bacteria or other genetically modified organisms, other drugs or components described herein, carriers used therewith for facilitating physical manipulations, or substantially any combinations thereof. Such identifiers may likewise function implicitly, such as by including a reservoir or dispenser identifier, a subroutine identifier, or some other such indirect parameter effective for selecting the bioactive material(s). This can occur, for example, in a context in which module 1500 has access to many doses of a desired formulation (inside a body 1240 of FIG. 12 larger than 1 milliliter, for example, or in such a module implanted in or borne by subject 1202). In some variants, moreover, processor 1540 may invoke logic for determining which dosage to administer in response to one or more recent measurements.

In some such contexts that implement system 1300, configuration module 1327 may perform operation 1613—configuring a decision module with one or more attributes of a bioactive mixture—by configuring one or more modules 1321-1323 with dosages or conditions under which a bioactive mixture is or is not to be administered. This information may be embodied in one or more parameters, values 1599, or other logic 1330 as described herein, for example. Instruction sequence 1316 may be operable for configuring processor 1390 to confirm that a subject was apparently exhaling within the last few seconds and currently appears to be inhaling, for example, based on audible, visual, thermal, and/or other suitable data detected in the subject's throat.

In some such contexts that implement system 1200 (of FIG. 12), one or more decision modules 1322, 1323 may be configured to perform one or more respective operations 1611, 1618, for selecting dispenser 1221 partly based on an indication of an urgent need for a drug and a designation of dispenser 1221 as the fastest mode (among two or more dispensing modes known to decision module 1323) suitable for addressing such need. Alternatively or additionally, such decision modules may be configured to indicate one or more specific valves, ports, modes, or other determinants as described herein for configuring one or more dispensers 1221. For insulin or other hormones, or hormone mimics, or for many other bioactive substances described herein, a formulation may be provided in a sufficiently concentrated form so that about 1 to 50 milligrams per day (or per dispensation) thereof is therapeutically effective. Such volumes are sufficient for treating a variety of pathologies according to existing inhaler regimens, for example, or for compliance with other physician-specified regimens, or for more appropriate responses to emergency situations. For a liquid formulation of this type, for example, dispenser 1221 may include a porous membrane through which a liquid formulation passes for aerosolization. A variety other suitable forms of dispenser 1221 are also readily implemented in light of teachings herein. See, e.g., U.S. Pat. No. 7,066,029 ("System and method for improved volume measurement"); U.S. Pat. No. 7,028,686 ("Inhaled insulin dosage control delivery enhanced by controlling total inhaled volume"); U.S. Pat. No. 6,889,690 ("Dry powder inhalers, related blister devices, and associated methods of dispensing dry powder substances and fabricating blister packages"); U.S. Pat. No. 6,655,379 ("Aerosolized active agent delivery").

Alternatively or additionally, gauge 1578 may be configured to perform operation 1723—indicating at least a remaining amount of one or more medicinal substances—by indicating such measurement data 1318 or other approximate remainders. In some variants, signaling module 1560 may be configured to signal user interface 1510 and/or a subject when an approximate amount remaining falls below a minimum threshold. In some such contexts, or more logic modules 1561 for generating a message or other value may be invoked to perform operation 1725—indicating at least one component containing one or more bioactive materials in the first wireless signal—by indicating one or more supplies 1307, 1308 or dispensers 1301-1303 in a wireless signal to user interface 1510. Alternatively or additionally, logic module 1563 may similarly be configured to perform operation 1728—confirming a selected dosage via the first wireless signal—by confirming a selected dosage (requested by user interface 1510 or administered to a subject, for example).

Some or all of the embodiments described herein may generally comprise technologies for handling one or more bioactive agents and/or carriers in releasable module form, via a liquid-bearing conduit, in a mist or other spray form, in a pumped or other pressurized form, or otherwise according to technologies described herein. In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to describe devices and/or processes in the fashion set forth herein, and thereafter use engineering practices to integrate such described devices and/or processes into image processing systems. That is, at least a portion of the devices and/or processes described herein can be integrated into an image processing system via a reasonable amount of experimentation. Those having skill in the art will recognize that a typical image processing system generally includes one or more of a system unit housing, a video display device, a memory such as volatile and non-volatile memory, processors such as microprocessors and digital signal processors, computational entities such as operating systems, drivers, and applications programs, one or more interaction devices, such as a touch pad or screen, control systems including feedback loops and control motors (e.g., feedback for sensing lens position and/or velocity; control motors for moving/distorting lenses to give desired focuses. A typical image processing system may be implemented utilizing any suitable commercially available components, such as those typically found in digital still systems and/or digital motion systems.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein can be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors (e.g., feedback for sensing position and/or velocity; control motors for moving and/or adjusting components and/or quantities). A typical data processing system may be implemented utilizing any suitable commercially available components, such as those typically found in data computing/communication and/or network computing/communication systems.

Those skilled in the art will recognize that it is common within the art to implement devices and/or processes and/or systems in the fashion(s) set forth herein, and thereafter use engineering and/or business practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, hovercraft, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a Voice over IP system, etc.), (f) a business entity (e.g., an Internet Service Provider (ISP) entity such as Comcast Cable, Quest, Southwestern Bell, etc), or (g) a wired/wireless services entity such as Sprint, Cingular, Nextel, etc.), etc.

One skilled in the art will recognize that the herein described components (e.g., steps), devices, and objects and the discussion accompanying them are used as examples for the sake of conceptual clarity and that various configuration modifications are within the skill of those in the art. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

With respect to the appended claims, those skilled in the art will appreciate that recited operations therein may generally be performed in any order. Examples of such alternate orderings may include overlapping, interleaved, interrupted, reordered, incremental, preparatory, supplemental, simultaneous, reverse, or other variant orderings, unless context dictates otherwise. With respect to context, even terms like "responsive to," "related to," or other past-tense adjectives are generally not intended to exclude such variants, unless context dictates otherwise.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A bioactive material administration system comprising:
   means for coupling two or more reservoirs containing one or more bioactive materials available for selection, the means for coupling enabling the two or more reservoirs to remain in a digestive tract for more than one day;
   means for implementing a selective dispensation of at least one bioactive material available for selection from the two or more reservoirs from within the digestive tract; and
   means for transmitting a first wireless signal indicating at least a bioactive material selection from within the digestive tract.

2. The bioactive material administration system of claim 1 in which the means for transmitting a first wireless signal indicating at least the bioactive material selection from within the digestive tract comprises:
   means for indicating at least a remaining amount of one or more medicinal substances.

3. The bioactive material administration system of claim 1 in which the means for transmitting a first wireless signal indicating at least the bioactive material selection from within the digestive tract comprises:
   means for indicating at least one component containing one or more bioactive materials in the first wireless signal.

4. The bioactive material administration system of claim 1 in which the means for transmitting a first wireless signal indicating at least the bioactive material selection from within the digestive tract comprises:
   means for confirming a selected dosage via the first wireless signal.

5. The bioactive material administration system of claim 2 in which the means for implementing a selective dispensation of at least one bioactive material available for selection from the two or more reservoirs from within the digestive tract comprises:
   means for receiving a second wireless signal including at least a device identifier as the bioactive material selection.

6. The bioactive material administration system of claim 1 in which the means for implementing a selective dispensation of at least one bioactive material available for selection from the two or more reservoirs from within the digestive tract comprises:
   means for configuring a decision module with one or more attributes of a bioactive mixture.

7. The bioactive material administration system of claim 1 in which the means for implementing a selective dispensation of at least one bioactive material available for selection from the two or more reservoirs from within the digestive tract comprises:
   means for activating a dispenser comprising at least one bioactive material and at least one other material.

8. The bioactive material administration system of claim 1 in which the means for a selective dispensation of at least one bioactive material available for selection from the two or more reservoirs from within the digestive tract comprises:
   means for signaling a decision of which port of a module to open in response to the bioactive material selection.

9. The bioactive material administration system of claim 1 in which the means for implementing a selective dispensation of at least one bioactive material available for selection from the two or more reservoirs from within the digestive tract comprises:
   means for dispensing at least an adhesive in response to the bioactive material selection.

10. The bioactive material administration system of claim 1 in which the means for transmitting a first wireless signal indicating at least the bioactive material selection from within the digestive tract comprises:
    means for detecting at least one substance indicative of the bioactive material selection.

11. The bioactive material administration system of claim 1 in which the means for implementing a selective dispensation of at least one bioactive material available for selection from the two or more reservoirs from within the digestive tract comprises:
  means for dispensing one or more of a hormone or a vasodilator.

12. The bioactive material administration system of claim 1 in which the means for implementing a selective dispensation of at least one bioactive material available for selection from the two or more reservoirs from within the digestive tract comprises:
  means for dispensing one or more of a pain reliever or an appetite suppressant.

13. The bioactive material administration system of claim 1 in which the means for implementing a selective dispensation of at least one bioactive material available for selection from the two or more reservoirs from within the digestive tract comprises:
  means for generating the bioactive material selection partly based on a substance detection and partly based on a device configuration.

14. The bioactive material administration system of claim 1 in which the means for transmitting a first wireless signal indicating at least the bioactive material selection from within the digestive tract comprises:
  means for indicating at least one pH-modifying material in the first wireless signal.

15. The bioactive material administration system of claim 14 in which the means for transmitting a first wireless signal indicating at least the bioactive material selection from within the digestive tract further comprises:
  means for indicating at least a remaining amount of one or more medicinal substances;
  means for indicating at least one component containing one or more bioactive materials in the first wireless signal; and
  means for confirming a selected dosage via the first wireless signal.

16. The bioactive material administration system of claim 15 in which the means for implementing a selective dispensation of at least one bioactive material available for selection from the two or more reservoirs from within the digestive tract comprises:
  means for receiving a second wireless signal including at least a device identifier as the bioactive material selection;
  means for configuring a decision module with one or more attributes of a bioactive mixture as the bioactive material selection;
  means for activating a dispenser comprising the bioactive mixture; and
  means for signaling a decision of which port of a module to open in response to the bioactive material selection.

17. The bioactive material administration system according to claim 14 in which the means for transmitting a first wireless signal indicating at least the bioactive material selection from within the digestive tract comprises:
  means for indicating at least a remaining amount of one or more medicinal substances.

18. The bioactive material administration system according to claim 11 in which the means for transmitting a first wireless signal indicating at least the bioactive material selection from within the digestive tract comprises:
  means for indicating at least one component containing one or more bioactive materials in the first wireless signal.

19. The bioactive material administration system according to claim 9 in which the means for transmitting a first wireless signal indicating at least the bioactive material selection from within the digestive tract comprises:
  means for confirming a selected dosage via the first wireless signal.

20. The bioactive material administration system according to claim 13 in which the means for implementing a selective dispensation of at least one bioactive material available for selection from the two or more reservoirs from within the digestive tract comprises:
  means for configuring a decision module with one or more attributes of a bioactive mixture.

21. The bioactive material administration system according to claim 8 in which the means for implementing a selective dispensation of at least one bioactive material available for selection from the two or more reservoirs from within the digestive tract comprises:
  means for activating a dispenser comprising at least one bioactive material and at least one other material.

22. The bioactive material administration system according to claim 14 in which the means for implementing a selective dispensation of at least one bioactive material available for selection from the two or more reservoirs from within the digestive tract comprises:
  means for signaling a decision of which port of a module to open in response to the bioactive material selection.

23. A bioactive material administration system comprising:
  circuitry for implementing a selective dispensation of at least one bioactive material available for selection from two or more reservoirs containing one or more bioactive materials from within a digestive tract, wherein the two or more reservoirs are configured to remain in the digestive tract for more than a day; and
  circuitry for transmitting a first wireless signal indicating at least the bioactive material selection from within the digestive tract.

24. The bioactive material administration system of claim 23 in which the circuitry for transmitting a first wireless signal indicating at least the bioactive material selection from within the digestive tract comprises:
  circuitry for indicating at least one component containing one or more bioactive materials in the first wireless signal.

25. The bioactive material administration system of claim 23 in which the circuitry for implementing a selective dispensation of at least one bioactive material available for selection from two or more reservoirs containing one or more bioactive materials from within a digestive tract, wherein the two or more reservoirs are configured to remain in the digestive tract for more than a day comprises:
  circuitry for receiving a second wireless signal including at least a device identifier as the bioactive material selection.

26. The bioactive material administration system of claim 23 in which the circuitry for implementing a selective dispensation of at least one bioactive material available for selection from two or more reservoirs containing one or more bioactive materials from within a digestive tract, wherein the two or more reservoirs are configured to remain in the digestive tract for more than a day comprises:
  circuitry for configuring a decision module with one or more attributes of a bioactive mixture.

27. The bioactive material administration system of claim 23 in which the circuitry for implementing a selective dispensation of at least one bioactive material available for selection from two or more reservoirs containing one or more bioactive materials from within a digestive tract, wherein the two or more reservoirs are configured to remain in the digestive tract for more than a day comprises:
 circuitry for signaling a decision of which port of a module to open in response to the bioactive material selection.

28. The bioactive material administration system of claim 23 in which the circuitry for implementing a selective dispensation of at least one bioactive material available for selection from two or more reservoirs containing one or more bioactive materials from within a digestive tract, wherein the two or more reservoirs are configured to remain in the digestive tract for more than a day comprises:
 circuitry for dispensing one or more of a hormone or a vasodilator.

29. The bioactive material administration system of claim 23 in which the circuitry for implementing a selective dispensation of at least one bioactive material available for selection from two or more reservoirs containing one or more bioactive materials from within a digestive tract, wherein the two or more reservoirs are configured to remain in the digestive tract for more than a day comprises:
 circuitry for dispensing one or more of a pain reliever or an appetite suppressant.

30. The bioactive material administration system of claim 23 further comprising:
 a module containing at least some of the circuitry for implementing a bioactive material selection from within a digestive tract.

31. A bioactive material administration system comprising:
 means for implementing a bioactive material selection from within a digestive tract;
 means for coupling two or more reservoirs containing one or more bioactive materials available for selection into at least one of a ring form or a tetrahedral form, the means for coupling enabling the two or more reservoirs to remain in a digestive tract for more than one day;
 means for activating a dispenser comprising at least one bioactive material and at least one other material; and
 means for transmitting a first wireless signal indicating at least the bioactive material selection from within the digestive tract.

32. A bioactive material administration system comprising:
 means for implementing a bioactive material selection from within a digestive tract;
 means for coupling two or more reservoirs containing one or more bioactive materials available for selection into at least one of a ring form or a tetrahedral form, the means for coupling enabling the two or more reservoirs to remain in a digestive tract for more than one day;
 means for transmitting a first wireless signal indicating at least the bioactive material selection from within the digestive tract;
 means for indicating at least one pH-modifying material in the first wireless signal;
 means for indicating at least a remaining amount of one or more medicinal substances;
 means for indicating at least one component containing one or more bioactive materials in the first wireless signal;
 means for confirming a selected dosage via the first wireless signal;
 means for receiving a second wireless signal including at least a device identifier as the bioactive material selection;
 means for configuring a decision module with one or more attributes of a bioactive mixture as the bioactive material selection;
 means for activating a dispenser comprising the bioactive mixture; and
 means for signaling a decision of which port of a module to open in response to the bioactive material selection.

33. The bioactive material administration system of claim 1 wherein the means for coupling two or more reservoirs containing one or more bioactive materials available for selection comprises:
 means for coupling two or more reservoirs containing one or more bioactive materials available for selection into at least one of a ring form or a tetrahedral form.

* * * * *

UNITED STATES PATENT AND TRADEMARK OFFICE
CERTIFICATE OF CORRECTION

| | | |
|---|---|---|
| PATENT NO. | : 8,808,276 B2 | Page 1 of 1 |
| APPLICATION NO. | : 10/536126 | |
| DATED | : August 19, 2014 | |
| INVENTOR(S) | : Boyden et al. | |

It is certified that error appears in the above-identified patent and that said Letters Patent is hereby corrected as shown below:

In the Claims

In Column 24, Line 24, Claim 5, delete "The bioactive material administration system of claim 2" and replace with --The bioactive material administration system of claim 1--

Signed and Sealed this
Thirteenth Day of January, 2015

Michelle K. Lee
*Deputy Director of the United States Patent and Trademark Office*